US011214811B1

(12) United States Patent
Nuccio et al.

(10) Patent No.: US 11,214,811 B1
(45) Date of Patent: Jan. 4, 2022

(54) INIR6 TRANSGENIC MAIZE

(71) Applicant: INARI AGRICULTURE TECHNOLOGY, INC., Cambridge, MA (US)

(72) Inventors: Michael Lee Nuccio, Salem, NH (US); Joshua L. Price, Cambridge, MA (US); Michael Andreas Kock, Rheinfelden (DE)

(73) Assignee: Inari Agriculture Technology, Inc., Cambridge, MA (US)

( * ) Notice: Subject to any disclaimer, the term of this patent is extended or adjusted under 35 U.S.C. 154(b) by 0 days.

(21) Appl. No.: 17/249,640

(22) Filed: Mar. 8, 2021

Related U.S. Application Data

(60) Provisional application No. 63/199,951, filed on Feb. 4, 2021, provisional application No. 63/059,813, filed on Jul. 31, 2020, provisional application No. 63/059,916, filed on Jul. 31, 2020, provisional application No. 63/059,860, filed on Jul. 31, 2020, provisional application No. 63/059,963, filed on Jul. 31, 2020, provisional application No. 63/199,930, filed on Feb. 3, 2021.

(51) Int. Cl.
*C12N 15/82* (2006.01)

(52) U.S. Cl.
CPC ...... *C12N 15/8213* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 7,632,985 B2 | 12/2009 | Malven et al. | |
| 8,232,456 B2 | 7/2012 | Long et al. | |
| 8,450,561 B2 | 5/2013 | Beazley et al. | |
| 8,575,434 B2 * | 11/2013 | Diehn | C12N 15/8279 800/302 |
| 9,540,655 B2 | 1/2017 | Cui et al. | |
| 2011/0191899 A1 * | 8/2011 | Ainley | C12N 15/8213 800/278 |
| 2015/0059010 A1 | 2/2015 | Cigan et al. | |
| 2015/0082478 A1 | 3/2015 | Cigan et al. | |
| 2018/0163218 A1 | 6/2018 | Corbin et al. | |
| 2019/0136249 A1 | 5/2019 | Sakai et al. | |
| 2019/0352655 A1 | 11/2019 | Niu et al. | |
| 2020/0157554 A1 | 5/2020 | Cigan et al. | |

OTHER PUBLICATIONS

Srivistava et al 2017 (Plant Cell Tiss Organ Cult 129: p. 153-160) (Year: 2017).*

Malzahn et al 2019 (BMC Biology 17:9 p. 1-14, published online Jan. 31, 2019) (Year: 2019).*

Bortesi et al., "The CRISPR/Cas9 system for plant genome editing and beyond", Biotechnology Advances, vol. 33, pp. 41-52, 2015.

Cho et al., "Nonallelic homologous recombination events responsible for copy number variation within an RNA silencing locus", Plant Direct, vol. 3, 16 pages, Aug. 5, 2019.

Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.

Srivastava et al., "Gene Stacking by recombinases", Plant Biotechnology Journal, vol. 14, pp. 471-482, 2016.

Xing et al., "Revealing frequent alternative polyadenylation and widespread low-level transcription read-through of novel plant transcription terminators", Plant Biotechnology Journal, vol. 8, pp. 772-782, 2010.

Young et al., "CRISPR-Cas9 Editing in Maize: Systematic Evaluation of Off-target Activity and Its Relevance in Crop Improvement", Scientific Reports, vol. 9, 11 pages, Apr. 15, 2019.

Du et al., "Construction of Marker-Free Genetically Modified Maize Using a Heat-Inducible Auto-Excision Vector", Genes, vol. 10, No. 374, pp. 1-17, 2019.

Que et al., "Maize transformation technology development for commercial event generation", Frontiers in Plant Science, vol. 5, Article 379, pp. 1-19, Aug. 2014.

Ward et al., "Petition for Determination of Nonregulated Status for Insect-Resistant MIR162 Maize", Syngenta, pp. 1-271, Aug. 31, 2007.

United States Patent and Trademark Office in connection with U.S. Appl. No. 17/248,936, filed Feb. 12, 2021, "Non-Final Office Action" 30 pages, dated Mar. 25, 2021.

Baliga et al., "Investigation of direct repeats, spacers and proteins associated with clustered regularly interspaced short palindromic repeat (CRISPR) system of Vibrio parahaemolyticus", Molecular Genetics and Genomics, vol. 294, pp. 253-262, 2019.

Kim et al., "CRISPR/Cpf1-mediated DNA-free plant genome editing", Nature Communications, vol. 8, No. 14406, pp. 1-20, Feb. 16, 2017.

Li et al., "Expanding the Scope of CRISPR/Cpf1-Mediated Genome Editing in Rice", Molecular Plant, vol. 11, pp. 995-998, Jul. 2018.

United States Patent and Trademark Office in connection with U.S. Appl. No. 17/302,739, filed May 11, 2021, "Non-Final Office Action", 29 pages, dated Aug. 3, 2021.

United States Patent and Trademark Office in connection with U.S. Appl. No. 17/302,110, filed Apr. 23, 2021, "Non-Final Office Action", 22 pages, dated Jun. 29, 2021.

United States Patent and Trademark Office in connection with U.S. Appl. No. 17/302,121, filed Apr. 23, 2021, "Non-Final Office Action", 10 pages, dated Jul. 8, 2021.

Ward, Dennis P., "Petition for Determination of Nonregulated Status for Insect-Resistant MIR162 Maize", Syngenta, pp. 1-268, Aug. 31, 2007.

(Continued)

*Primary Examiner* — Matthew R Keogh

(74) *Attorney, Agent, or Firm* — McKee, Voorhees & Sease, PLC

(57) ABSTRACT

Transgenic INIR6 maize plants comprising modifications of the DP-4114 maize locus which provide for facile excision of the modified DP-4114 transgenic locus or portions thereof, methods of making such plants, and use of such plants to facilitate breeding are disclosed.

4 Claims, 26 Drawing Sheets

Figure 1D:
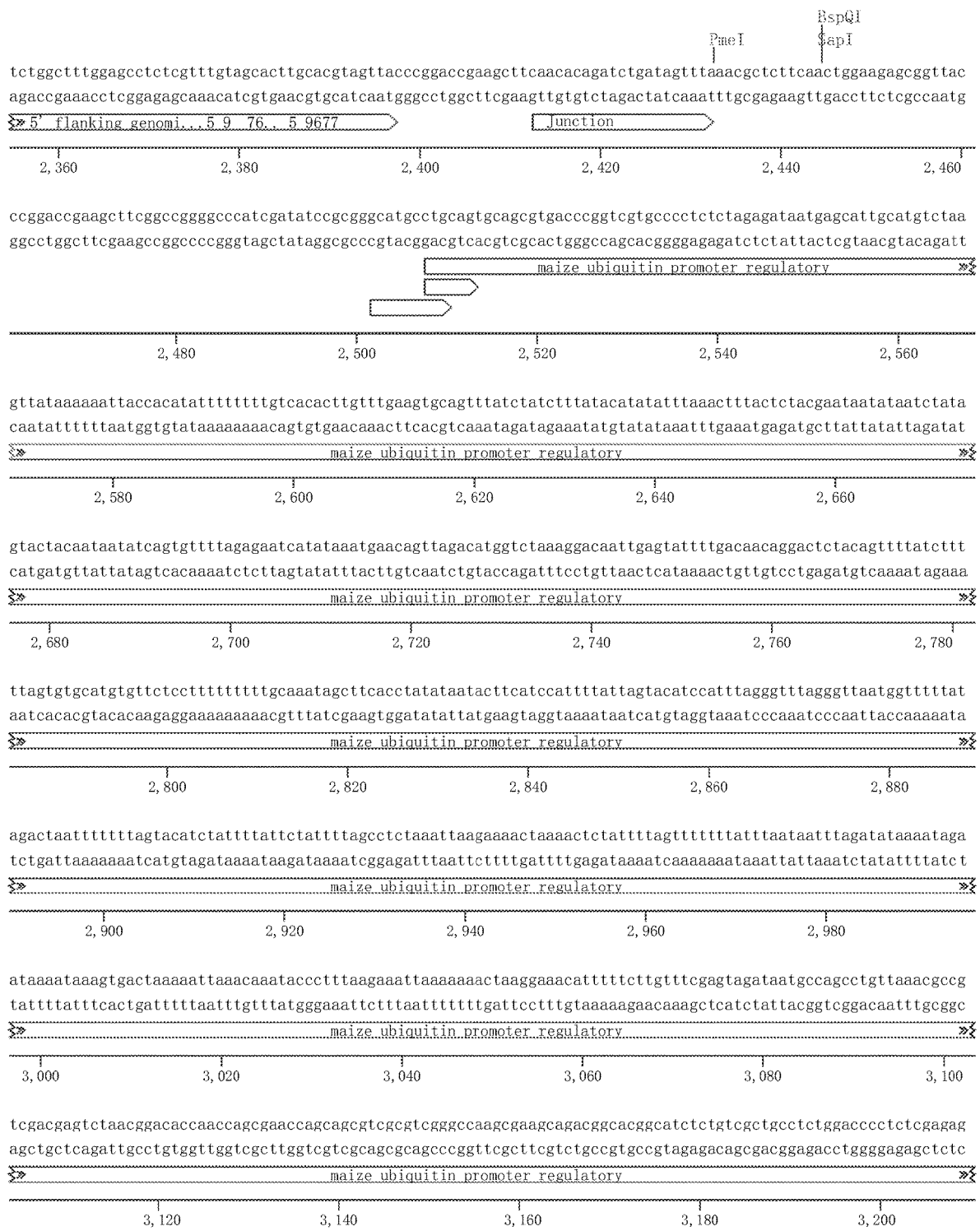

Specification includes a Sequence Listing.

(56) References Cited

OTHER PUBLICATIONS

International Searching Authority in connection with PCT/US21/43945 filed Jul. 20, 2021, "Invitation to Pay Additional Fees And, Where Applicable, Protest Fee", 4 pages, dated Oct. 27, 2021.
International Searching Authority in connection with PCT/US21/43935 filed Jul. 30, 2021, "Invitation to Pay Additional Fees And, Where Applicable, Protest Fee", 3 pages, dated Oct. 26, 2021.
Finnigan et al., "mCAL: A New Approach for Versatile Multiplex Action of Cas9 Using One sgRNA and Loci Flanked by a Programmed Target Sequence", G3, vol. 6, pp. 2147-2156, Jul. 2016.
International Searching Authority in connection with PCT/US21/43897 filed Jul. 30, 2021, "Invitation to Pay Additional Fees And, Where Applicable, Protest Fee", 3 pages, dated Oct. 27, 2021.

\* cited by examiner

DP-4114_(DP-004114-3) (16752 bp)

```
                                     Baer
                                      |
gagcatatccagcaccagctggtaccaaggtcgggtctctgtgctagtgctattagctagtgtaaggagcgagtaggtcagttaaggctggtgcgtcgtgagggctg
ctcgtataggtcgtggtcgaccatggttccagcccagagacacgatcacgataatcgatcacattcctcgctcatccagtcaattccgaccacgcagcactcccgac
         5' flanking genomic sequence Chr1:15194376..15196773
         |              |              |              |              |
        20             40             60             80            100 tcttgtgtgtagctacagcagacggttcatcagaaggattattcgtgcagtatatacagtacaactagacaatgatgttgatgattggtctagagctagaggcctat
agaacacacatcgatgtcgtctgccaagtagtcttcctaataagcacgtcatatatgtcatgttgatctgttactacaactactaaccagatctcgatctccggata
                        5' flanking genomic sequence Chr1:15194376..15196773
         |              |              |              |              |
       120            140            160            180            200 agccctatactactgtgtattgtccgccgttttagttttttggtcccatccatcaatgcaaccgccttgttttgctccaattgtcccgttcctgcgcctcgctttt
tcgggatatgatgacacataacaggcggcaaaatcaaaaaaccagggtagggtagttacgttggcggaacaaaacgaggttaacagggcaaggacgcggagcgaaaa
                        5' flanking genomic sequence Chr1:15194376..15196773
         |              |              |              |              |
       220            240            260            280            300            320

Nrur
                                                                                               |
gctctgtcgcatcgcatacaaaaaaaaaaacgccgcgccggctttgaatcgcgcccccaactgctccaaccaggcaacggacacggccaccgtccgtgtcgcgagc
cgagacagcgtagcgtatgttttttttttttgcggcgcggccgaaacttagcgcgggggttgacgaggttggtccgttgcctgtgccggtggcaggcacagcgctcg
                        5' flanking genomic sequence Chr1:15194376..15196773
         |              |              |              |              |
       340            360            380            400            420 aaaaaaacaaaaagaggaacgcgtccaggacgaagcagtccactgccgctgtggccggcaaaagatctggttgagcacatggagattggagaaggttggttggttct
ttttttttgttttttctccttgcgcaggtcctgcttcgtcaggtgacggcgacaccggccgttttctagaccaactcgtgtacctctaacctcttccaaccaacaaga
                        5' flanking genomic sequence Chr1:15194376..15196773
         |              |              |              |              |
       440            460            480            500            520 tctggaaacgccaatgaatgggggcactgacatgtactcttaacatgtagtgcaatccagagatcggatatccagacactggcagcacgatcgcctcgcgccgtaga
agacctttgcggttacttaccccgtgactgtacatgagaattgtacatcacgttaggtctctagcctataggtctgtgaccgtcgtgctagcggagcgcggcatct
                        5' flanking genomic sequence Chr1:15194376..15196773
         |              |              |              |              |
       540            560            580            600            620            640 tcacgcacgcaaattactgaagaccattcacaaaaaaaaaaaaacacacaggggctagcgtgcccacaccaaacccaagtgctgcgttgcacgcaggggagcgaaa
agtgcgtgcgtttaatgacttctggtaagtgtttttttttttttgtgtgtccccgatcgcacggggtgtggtttgggttcacgacgcaacgtgcgtcccctcgcttt
                        5' flanking genomic sequence Chr1:15194376..15196773
         |              |              |              |              |
       660            680            700            720            740
```

FIG. 1A

```
                                                                                               BstAPI
aaaaacaataatgctcactgtcacgtcgcgtatccaaccccgcggacgtctcggctctcagcagcagcacacggggcacctcacgatgccgttctcgttgcactccg
ttttgttattacgagtgacagtgcagcgcatagg ttggggcgcctgcagagccgagagtcgtcgtcgtgtgccccgtggagtgctacggcaagagcaacgtgaggc
         5' flanking genomic sequence Chr1:15194376..15196773
    760        780        800        820        840 tgcaccgccggaacccgccgccgcattcgtcgccctcctcctcctcctccgcctcgtcttcgtcacccacgtacaccttgcagctgcccgagcagacatcgcagagc
acgtggcggccttgggcggcggcgtaagcagcggggaggaggaggaggaggcggagcagaagcagtgggtgcatgtggaacgtcgacggctcgtctgtagcgtctcg
         5' flanking genomic sequence Chr1:15194376..15196773
    860        880        900        920        940        960

SgrAI
                        MreI            FseI
acgaaccgcatgtccccgcaggcctcgcacgcgccggcgtcgccgccgtgtgggccggccgtcgacgcagcgctctcgcaccggccagcctcggcgcgagctcccc
tgcttggcgtacaggggcgtccggagcgtgcgcggccgcagcggcggcacacccggccggcagctgcgtcgcgagagcgtgggccggtcggagccgcgctcgagggg
         5' flanking genomic sequence Chr1:15194376..15196773
    980       1,000      1,020      1,040      1,060 ggcctcgtgcagccgcttcagctcctcggcgttgcccacgagctccccgtccacgaagaggctggggagggcggcgggcgtgccgccggcttggccgagcccgaggc
ccggagcacgtcggcgaagtcgaggagccgcaacgggtgctcgaggggcaggtgcttctccgaccctcccgccgcccgcacggcggccgaaccggctcgggctccg
         5' flanking genomic sequence Chr1:15194376..15196773
   1,080      1,100      1,120      1,140      1,160 cgagaaggccgcggagctcgtcccggaacccgcggtgcatggacacgtcgcgctcgtcgaggcgcacgccgtagcccttgaggatggcgcgcgccaggcagcagtcc
gctcttccggcgcctcgagcagggccttgggcgccacgtacctgtgcagcgcgagcagctccgcgtgcggcatcgggaactcctaccgcgcgcggtccgtcgtcagg
         5' flanking genomic sequence Chr1:15194376..15196773
   1,180      1,200      1,220      1,240      1,260      1,280 tcgtgcgtggcgcgcacgccgcgcagcgacgtgaagtagagcaccgccctccgcggcggcagcgcctttcccctccccgccgctcgtcggggcggcgtcgggccgagg
agcacgcaccgcgcgtgcggcgcgtcgctgcacttcatctcgtggcgggaggcgccgccgtcgcggaaggggaggggcggcgagcagccccgccgcagcccggctcc
         5' flanking genomic sequence Chr1:15194376..15196773
   1,300      1,320      1,340      1,360      1,380

AscI
catcggcatcggcagcggcgtcaccttggcggacgccgcgaggtcctgcgcaggcgccgtggcgaccgggaacgagaaggagtggcgcccgaacgcgcgcgcccagca
gtagccgtagccgtcgccgcagtggaaccgcctgcggcgctccaggacgcgtccgcggcaccgctggcccttgctcttcctcaccgcgggcttgccgcgcgggtcgt
         5' flanking genomic sequence Chr1:15194376..15196773
   1,400      1,420      1,440      1,460      1,480
```

FIG. 1B

```
                    FseI
                    |
gcggggagcggtcctcgaggccggccatgagcgcccacgcgtcgatgtcctcgggctcgttgggcggcgtcatggtgggcgtgcgcggcgccagcctcgtgggcgcg
cgcccctcgccaggagctccggccggtactcgcgggtgcgcagctacaggagcccgagcaacccgccgcagtaccacccgcacgcgccgcggtcggagcacccgcgc
```
⟫──────── 5' flanking genomic sequence Chr1:15194376..15196773 ────────⟪
```
1,500        1,520        1,540        1,560        1,580        1,600
```

```
                  KflI
                  |
ggctccggcgcccgcggcagggccttgtccagctccagggacccgagcgtggacgacgtgagccgcaccacgtggacgccgacgtcgctggggcaccgagccgggaa
ccgaggccgcgggcgccgtcccggaacaggtcgaggtccctgggctcgcacctgctgcactcggcgtggtgcacctgcggctgcagcgaccccgtggctcggcccttt
```
⟫──────── 5' flanking genomic sequence Chr1:15194376..15196773 ────────⟪
```
       1,620        1,640        1,660        1,680        1,700
```

```
cgactggctgcgcggcagcggtgacgggcagtaccggaggtcgtgacgggcctgccttgaggtggtgcaccccatggcaccaatgtacacacacggccaaagcgcca
gctgaccgacgcgccgtcgccactgcccgtcatggcctccagcactgcccggacggaactccaccacgtggggtaccgtggttacatgtgtgtgccggtttcgcggt
```
⟫──────── 5' flanking genomic sequence Chr1:15194376..15196773 ────────⟪
```
1,720        1,740        1,760        1,780        1,800
```

```
agtgggctgcagactgcctgccaatgtgatcaagcagccaggagcagagacggatctctggggatcggggtttctggggtttaggatctttatactactctgtcatt
tcacccgacgtctgacggacggttacactagttcgtcggtcctcgtctctgcctagagacccctagccccaaagaccccaaatcctagaaatatgatgagacagtaa
```
⟫──────── 5' flanking genomic sequence Chr1:15194376..15196773 ────────⟪
```
1,820        1,840        1,860        1,880        1,900        1,920
```

```
ggggatataaaactaggagtgtggttaattaggactcgatagataagtttaccacaagcgcgtgaaatggtctacccgatgatgtgattggcctaaaaagaacaaga
cccctatattttgatcctcacaccaattaatcctgagctatctattcaaatggtgttcgcgcactttaccagatgggctactacactaaccggatttttcttgttct
```
⟫──────── 5' flanking genomic sequence Chr1:15194376..15196773 ────────⟪
```
       1,940        1,960        1,980        2,000        2,020
```

```
agagtatttggagctactgaacattctcttttcctgaagataactaattttggaacattcagacttgggagtctggacttttggagggaagttcaaattgtggtct
tctcataaacctcgatgacttgtaagagaaaaggacttctattgattaaaaaccttgtaagtctgaaccctcagacctgaaaacctcccttcaagtttaacaccaga
```
⟫──────── 5' flanking genomic sequence Chr1:15194376..15196773 ────────⟪
```
2,040        2,060        2,080        2,100        2,120        2,140
```

```
gcctctgccatgtgttgttttttagtcggagagtggccctcatttttttgtcctgtttagctttatagtcgtagcagctagtagcgaaatttaaccttggattatg
cggagacggtacacaacaaaaaatcagcctctcaccgggagtaaaaaaaacaggacaaatcgaaatatcagcatcgtcgatcatcgctttaaattggaacctaatac
```
⟫──────── 5' flanking genomic sequence Chr1:15194376..15196773 ────────⟪
```
       2,160        2,180        2,200        2,220        2,240
```

```
gccgtgttagtcaaacaatcattgatttatttcctcccttttcgcgctgcttttcctgtacgcatctccgctgcccttgattcgaggaccctgttcacaacacagggc
cggcacaatcagtttgttagtaactaaataaggagggaaagcgcgacgaaaaggacatgcgtagaggcgacgggaactaagctcctgggacaagtgttgtgtcccg
```
⟫──────── 5' flanking genomic sequence Chr1:15194376..15196773 ────────⟪
```
2,260        2,280        2,300        2,320        2,340
```

FIG. 1C

```
ttccgctccaccgttggacttgctccgctgtcggcatccagaaattgcgtggcggagcggcagacgtgagccggcacggcaggcggcctcctcctcctctcacggca
aaggcgaggtggcaacctgaacgaggcgacagccgtaggtctttaacgcaccgcctcgccgtctgcactcggccgtgccgtccgccggaggaggaggagagtgccgt
```
maize ubiquitin promoter regulatory 3,220    3,240    3,260    3,280    3,300

```
ccggcagctacgggggattcctttcccaccgctccttcgctttccttcctcgcccgccgtaataaatagacacccctccacaccctctttccccaacctcgtgtt
ggccgtcgatgccccctaaggaaagggtggcgaggaagcgaaagggaaggagcgggcggcattatttatctgtgggggaggtgtgggagaaaggggttggagcacaa
```
maize ubiquitin promoter regulatory
Ubi1 5' UTR 3,320    3,340    3,360    3,380    3,400    3,420

```
gttcggagcgcacacacacacaaccagatctcccccaaatccacccgtcggcacctccgcttcaaggtacgccgctcgtcctccccccccccccctctctaccttct
caagcctcgcgtgtgtgtgtgttggtctagagggggtttaggtgggcagccgtggaggcgaagttccatgcggcgagcaggagggggggggggggagagatggaaga
```
ubi1; maize ubiquitin intron
Ubi1 5' UTR
maize ubiquitin promoter regulatory
Maize Ubi intron
Ubi1 5' UTR
Maize Ubi gene 3,440    3,460    3,480    3,500    3,520

```
ctagatcggcgttccggtccatggttagggcccggtagttctacttctgttcatgtttgtgttagatccgtgtttgtgttagatccgtgctgctagcgttcgtacac
gatctagccgcaaggccaggtaccaatcccgggccatcaagatgaagacaagtacaaacacaatctaggcacaaacacaatctaggcacgacgatcgcaagcatgtg
```
ubi1; maize ubiquitin intron
Ubi1 5' UTR
maize ubiquitin promoter regulatory
Maize Ubi intron
Maize Ubi gene 3,540    3,560    3,580    3,600    3,620

```
ggatgcgacctgtacgtcagacacgttctgattgctaacttgccagtgtttctctttggggaatcctgggatggctctagccgttccgcagacgggatcgatttcat
cctacgctggacatgcagtctgtgcaagactaacgattgaacggtcacaaagagaaaccccttaggaccctaccgagatcggcaaggcgtctgccctagctaaagta
```
ubi1; maize ubiquitin intron
Ubi1 5' UTR
maize ubiquitin promoter regulatory
Maize Ubi intron
Maize Ubi gene 3,640    3,660    3,680    3,700    3,720    3,740

```
gatttttttgtttcgttgcatagggtttggtttgccctttttcctttatttcaatatatgccgtgcacttgtttgtcgggtcatcttttcatgctttttttttgtctt
ctaaaaaaaacaaagcaacgtatcccaaaccaaacgggaaaaggaaataaagttatatacggcacgtgaacaaacagcccagtagaaaagtacgaaaaaaaacagaa
```
ubi1; maize ubiquitin intron
Ubi1 5' UTR
maize ubiquitin promoter regulatory
Maize Ubi intron
Maize Ubi gene 3,760    3,780    3,800    3,820    3,840

FIG. 1E ggttgtgatgatgtggtctggttgggcggtcgttctagatcggagtagaattctgtttcaaactacctggtggatttattaattttggatctgtatgtgtgtgccat
ccaacactactacaccagaccaacccgccagcaagatctagcctcatcttaagacaaagtttgatggaccacctaaataattaaaacctagacatacacacacggta

| ubi1; maize ubiquitin intron |
| Ubi1 5' UTR |
| maize ubiquitin promoter regulatory |
| Maize Ubi intron |
| Maize Ubi gene |

3,860    3,880    3,900    3,920    3,940 acatattcatagttacgaattgaagatgatggatggaaatatcgatctaggataggtatacatgttgatgcgggttttactgatgcatatacagagatgctttttgt
tgtataagtatcaatgcttaacttctactacctacctttatagctagatcctatccatatgtacaactacgcccaaaatgactacgtatatgtctctacgaaaaaca

| ubi1; maize ubiquitin intron |
| Ubi1 5' UTR |
| maize ubiquitin promoter regulatory |
| Maize Ubi intron |
| Maize Ubi gene |

3,960    3,980    4,000    4,020    4,040    4,060 tcgcttggttgtgatgatgtggtgtggttgggcggtcgttcattcgttctagatcggagtagaatactgtttcaaactacctggtgtatttattaattttggaactg
agcgaaccaacactactacaccacaccaacccgccagcaagtaagcaagatctagcctcatcttatgacaaagtttgatggaccacataaataattaaaaccttgac

| ubi1; maize ubiquitin intron |
| Ubi1 5' UTR |
| maize ubiquitin promoter regulatory |
| Maize Ubi intron |
| Maize Ubi gene |

4,080    4,100    4,120    4,140    4,160 tatgtgtgtgtcatacatcttcatagttacgagtttaagatggatggaaatatcgatctaggataggtatacatgttgatgtgggttttactgatgcatatacatga
atacacacacagtatgtagaagtatcaatgctcaaattctacctacctttatagctagatcctatccatatgtacaactacacccaaaatgactacgtatatgtact

| ubi1; maize ubiquitin intron |
| Ubi1 5' UTR |
| maize ubiquitin promoter regulatory |
| Maize Ubi intron |
| Maize Ubi gene |

4,180    4,200    4,220    4,240    4,260    4,280 tggcatatgcagcatctattcatatgctctaaccttgagtacctatctattataataaacaagtatgttttataattattttgatcttgatatacttggatgatggc
accgtatacgtcgtagataagtatacgagattggaactcatggatagataatattatttgttcatacaaaatattaataaaactagaactatatgaacctactaccg

| ubi1; maize ubiquitin intron |
| Ubi1 5' UTR |
| maize ubiquitin promoter regulatory |
| Maize Ubi intron |
| Maize Ubi gene |

4,500    4,520    4,540    4,560    4,580

FIG. 1F atatgcagcagctatatgtggatttttttagccctgccttcatacgctatttatttgcttggtactgtttcttttgtcgatgctcaccctgttgtttggtgttactt
tatacgtcgtcgatatacacctaaaaaaatcgggacggaagtatgcgataaataaacgaaccatgacaaagaaaacagctacgagtgggacaacaaaccacaatgaa ubi1; maize ubiquitin intron
Ubi1 5' UTR
maize ubiquitin promoter regulatory
Maize Ubi intron
Maize Ubi gene 4,400    4,420    4,440    4,460    4,480 ctgcaggtcgactctagaggatccaacaatggagaacaacatacagaatcagtgcgtccctacaactgcctcaacaatcctgaagtagagattctcaacgaagaga
gacgtccagctgagatctcctaggttgttacctcttgttgtatgtcttagtcacgcaggggatgttgacggagttgttaggacttcatctctaagagttgcttctct Omega...tory
cry1F protein 4,500    4,520    4,540    4,560    4,580    4,600 ggtcgactggcagattgccgttagacatctccctgtcccttacacgtttcctgttgtctgagtttgttccaggtgtgggagttgcgtttggcctcttcgacctcatc
ccagctgaccgtctaacggcaatctgtagagggacagggaatgtgcaaaggacaacagactcaaacaaggtccacaccctcaacgcaaaccggagaagctggagtag cry1F protein 4,620    4,640    4,660    4,680    4,700

EcoNI tggggcttcatcactccatctgattggagcctctttcttctccagattgaacagttgattgaacaaaggattgagaccttggaaaggaatcgggccatcactaccct
accccgaagtagtgaggtagactaacctcggagaaagaaggaggtctaacttgtcaactaacttgtttcctaactctggaacctttccttagcccggtagtgatggga cry1F protein 4,720    4,740    4,760    4,780    4,800

BlpI tcgtggcttagcagacagctatgagatctacattgaagcactaagagagtgggaagccaatcctaacaatgcccaactgagagaagatgtgcgtatacgctttgcta
agcaccgaatcgtctgtcgatactctagatgtaacttcgtgattctctcacccttcggttaggattgttacggggttgactctcttctacacgcatatgcgaaacgat cry1F protein 4,820    4,840    4,860    4,880    4,900    4,920 acacagatgatgctttgatcacagccatcaacaacttcaccccttaccagcttcgagatccctcttctctcggtctatgttcaagctgctaacctgcacttgtcacta
tgtgtctactacgaaactagtgtcggtagttgttgaagtgggaatggtcgaagctctagggagaagagagccagatacaagttcgacgattggacgtgaacagtgat cry1F protein 4,940    4,960    4,980    5,000    5,020 ctgcgcgacgctgtgtcgtttgggcaaggttggggactggacatagctactgtcaacaatcactacaacagactcatcaatctgattcatcgatacacgaaacattg
gacgcgctgcgacacagcaaacccgttccaaccctgacctgtatcgatgacagttgttagtgatgttgtctgagtagttagactaagtagctatgcctttgtaac cry1F protein 5,040    5,060    5,080    5,100    5,120

FIG. 1G

```
tttggatacctacaatcagggattggagaacctgagaggtactaacactcgccaatgggccaggttcaatcagttcaggagagaccttacacttactgtgttagaca
aaacctatggatgttagtccctaacctcttggactctccatgattgtgagcggttacccggtccaagttagtcaagtcctctctggaatgtgaatgacacaatctgt
```

```
├≫──────────────────────── cryIF protein ─────────────────────────≫┤
  5,140        5,160        5,180        5,200        5,220        5,240
```

```
tagttgctctctttccgaactacgatgttcgtacctatccgattcaaacgtcatcccaacttacaagggagatctacaccagttcagtcattgaagactctccagtt
atcaacgagagaaaggcttgatgctacaagcatggataggctaagtttgcagtagggttgaatgttccctctagatgtggtcaagtcagtaacttctgagaggtcaa
```

```
├≫──────────────────────── cryIF protein ─────────────────────────≫┤
        5,260        5,280        5,300        5,320        5,340
```

```
tctgcgaacatacccaatggtttcaacagggctgagtttggagtcagaccaccccatctcatggacttcatgaactctttgtttgtgactgcagagactgttagatc
agacgcttgtatgggttaccaaagttgtcccgactcaaacctcagtctggtggggtagagtacctgaagtacttgagaaacaaacactgacgtctctgacaatctag
```

```
├≫──────────────────────── cryIF protein ─────────────────────────≫┤
  5,360        5,380        5,400        5,420        5,440
```

```
ccaaactgtgtggggaggacacttagttagctcacgcaacacggctggcaatcgtatcaactttcctagttacggggtcttcaatcccggggggcgccatctggattg
ggtttgacacaccccctcctgtgaatcaatcgagtgcgttgtgccgaccgttagcatagttgaaaggatcaatgccccagaagttagggcccccgcggtagacctaac
```

```
├≫──────────────────────── cryIF protein ─────────────────────────≫┤
        5,460        5,480        5,500        5,520        5,540        5,560
```

```
cagatgaagatccacgtcctttctatcggaccttgtcagatcctgtcttcgtccgaggaggctttggcaatcctcactatgtactcggtcttaggggagtggcctttt
gtctacttctaggtgcaggaaagatagcctggaacagtctaggacagaagcaggctcctccgaaaccgttaggagtgatacatgagccagaatcccctcaccggaaa
```

```
├≫──────────────────────── cryIF protein ─────────────────────────≫┤
        5,580        5,600        5,620        5,640        5,660
```

```
caacaaactggtacgaatcacacccgcacattcaggaactccgggaccattgactctctagatgagataccacctcaagacaacagcggcgcaccttggaatgacta
gttgtttgaccatgcttagtgtgggcgtgtaagtccttgaggccctggtaactgagagatctactctatggtggagttctgttgtcgccgcgtggaaccttactgat
```

```
├≫──────────────────────── cryIF protein ─────────────────────────≫┤
        5,680        5,700        5,720        5,740        5,760
```

```
ctcccatgtgctgaatcatgttacctttgtgcgctggccaggtgagatctcaggttccgactcatggagagcaccaatgttctcttggacgcatcgtagcgctaccc
gagggtacacgacttagtacaatggaaacacgcgaccggtccactctagagtccaaggctgagtacctctcgtggttacaagagaacctgcgtagcatcgcgatggg
```

```
├≫──────────────────────── cryIF protein ─────────────────────────≫┤
  5,780        5,800        5,820        5,840        5,860        5,880
```

```
ccacaaacaccattgatccagagagaatcactcagattcccttggtgaaggcacacacacttcagtcaggaactacagttgtaagagggcgggggttcacgggagga
ggtgtttgtggtaactaggtctctcttagtgagtctaagggaaccacttccgtgtgtgtgaagtcagtccttgatgtcaacattctcccggccccaagtgccctcct
```

```
├≫──────────────────────── cryIF protein ─────────────────────────≫┤
        5,900        5,920        5,940        5,960        5,980
```

FIG. 1H

```
gacattcttcgacgcactagtggaggaccattcgcgtacaccattgtcaacatcaatgggcaacttccccaaaggtatcgtgccaggatacgctatgcctctactac
ctgtaagaagctgcgtgatcacctcctggtaagcgcatgtggtaacagttgtagttacccgttgaaggggtttccatagcacggtcctatgcgatacggagatgatg
``` cry F protein 6,000　　　　6,020　　　　6,040　　　　6,060　　　　6,080

AgeI

```
caatctaagaatctacgttacggttgcaggtgaacggatctttgctggtcagttcaacaagacaatggataccggtgatccacttacattccaatctttctcctacg
gttagattcttagatgcaatgccaacgtccacttgcctagaaacgaccagtcaagttgttctgttacctatggccactaggtgaatgtaaggttagaaagaggatgc
``` cry F protein 6,100　　6,120　　6,140　　6,160　　6,180　　6,200

```
ccactatcaacaccgcgttcacctttccaatgagccagagcagtttcacagtaggtgctgataccttcagttcaggcaacgaagtgtacattgacaggtttgagttg
ggtgatagttgtggcgcaagtggaaaggttactcggtctcgtcaaagtgtcatccacgactatggaagtcaagtccgttgcttcacatgtaactgtccaaactcaac
``` cry F protein 6,220　　　　6,240　　　　6,260　　　　6,280　　　　6,300

NruI

```
attccagttactgccacactcgagtaaggatccgtcgacctgcagccaagctttcgcgagctcgagatccccgacatatgccccggtttcgttgcgactaacatgag
taaggtcaatgacggtgtgagctcattcctaggcagctggacgtcggttcgaaagcgctcgagctctaggggctgtatacggggccaaagcaacgctgattgtactc
``` cry F protein 6,320　　　　6,340　　　　6,360　　　　6,380　　　　6,400　　　　6,420

```
ttcttggacaaatttgattggacctgatgagatgatccaacccgaggatatagcaaagctcgttcgtgcagcaatggaacggccaaaccgtgcttttgtccccaaga
aagaacctgtttaaactaacctggactactctactaggttgggctcctatatcgtttcgagcaagcacgtcgttaccttgccggtttggcacgaaaacaggggttct
```

6,440　　6,460　　6,480　　6,500　　6,520

```
atgaggtgctatgcatgaaggaatctacccgttgatgtccaacagtctcagggttaatgtctatgtatcttaaataatgttgtcggtattttgtaatctcatataga
tactccacgatacgtacttccttagatgggcaactacaggttgtcagagtcccaattacagatacatagaatttattacaacagccataaaacattagagtatatct
```

6,540　　　　6,560　　　　6,580　　　　6,600　　　　6,620

```
ttttcactgtgcgacgcaaaaatattaaataaatattattattatctacgttttgattgagatatcatcaatattataataaaaatatccattaaacacgatttgat
aaaagtgacacgctgcgttttataatttatttataataataatagatgcaaaactaactctatagtagttataatattatttttataggtaatttgtgctaaacta
```

6,640　　6,660　　6,680　　6,700　　6,720　　6,740

```
acaaatgacagtcaataatctgatttgaatatttattaattgtaacgaattacataaagatcgaatagaaaatactgcactgcaaatgaaaattaacacatactaat
tgtttactgtcagttattagactaaacttataaataattaacattgcttaatgtatttctagcttatcttttatgacgtgacgtttacttttaattgtgtatgatta
```

6,760　　　6,780　　　6,800　　　6,820　　　6,840

```
aaatgcgtcaaatatctttgccaagatcaagcggagtgagggcctcatatccggtctcagttacaagcacggtatccccgaagcgcgctccaccaatgccctcgaca
tttacgcagtttatagaaacggttctagttcgcctcactcccggagtataggccagagtcaatgttcgtgccataggggcttcgcgcgaggtggttacgggagctgt
```

6,860　　　6,880　　　6,900　　　6,920　　　6,940

FIG. 1I

```
                BbvCI
                |
tagatgccgggctcgacgctgaggacattgcctaccttgagcatggtctcagcgccggctttaagctcaatcccatcccaatctgaatatcctatcccgcgcccagt
atctacggcccgagctgcgactcctgtaacggatggaactcgtaccagagtcgcggccgaaattcgagttagggtagggttagacttataggataggggcgcgggtca
---------|-----------------|-----------------|-----------------|-----------------|-----------------|-----------
      6,960              6,980             7,000             7,020             7,040             7,060 ccggtgtaagaacgggtctgtccatccacctctgttgggaattccggtccgggtcacctttgtccaccaagatggaactgcggccagcttgcatgcctgcagtgcag
ggccacattcttgcccagacaggtaggtggagacaacccttaaggccaggcccagtggaaacaggtggttctaccttgacgccggtcgaacgtacggacgtcacgtc
                                                                                                    [ ma..y >>]
                                                                                                    └──────>
---------|-----------------|-----------------|-----------------|-----------------|-----------------|-----------
      7,080              7,100             7,120             7,140                              7,160 cgtgacccggtcgtgcccctctctagagataatgagcattgcatgtctaagttataaaaaattaccacatattttttttgtcacacttgtttgaagtgcagtttatc
gcactgggccagcacggggagagatctctattactcgtaacgtacagattcaatatttttttaatggtgtataaaaaaaacagtgtgaacaaacttcacgtcaaatag
[>>.................................... maize ubiquitin promoter regulatory ............................>>]
---------|-----------------|-----------------|-----------------|-----------------|-----------------|-----------
      7,180              7,200             7,220             7,240             7,260 tatctttatacatatatttaaactttactctacgaataatataatctatagtactacaataatatcagtgttttagagaatcatataaatgaacagttagacatggt
atagaaatatgtatataaatttgaaatgagatgcttattatattagatatcatgatgttattatagtcacaaaatctcttagtatatttacttgtcaatctgtacca
[>>.................................... maize ubiquitin promoter regulatory ............................>>]
---------|-----------------|-----------------|-----------------|-----------------|-----------------|-----------
      7,280              7,300             7,320             7,340             7,360             7,380 ctaaaggacaattgagtattttgacaacaggactctacagttttatcttttagtgtgcatgtgttctccttttttttttgcaaatagcttcacctatataatacttc
gatttcctgttaactcataaaactgttgtcctgagatgtcaaaatagaaaaatcacacgtacacaagaggaaaaaaaacgtttatcgaagtggatatattatgaag
[>>.................................... maize ubiquitin promoter regulatory ............................>>]
---------|-----------------|-----------------|-----------------|-----------------|-----------------|-----------
      7,400              7,420             7,440             7,460             7,480 atccattttattagtacatccatttagggtttagggttaatggttttttatagactaattttttagtacatctattttattctattttagcctctaaattaagaaaa
taggtaaaataatcatgtaggtaaatcccaaatcccaattaccaaaaatatctgattaaaaaaatcatgtagataaaataagataaatcggagatttaattctttt
[>>.................................... maize ubiquitin promoter regulatory ............................>>]
---------|-----------------|-----------------|-----------------|-----------------|-----------------|-----------
      7,500              7,520             7,540             7,560             7,580 ctaaaactctattttagttttttttatttaataatttagatataaaatagaataaaataaagtgactaaaaattaaacaaatacccttaagaaattaaaaaaactaa
gattttgagataaaatcaaaaaaataaattattaaatctatattttatcttattttatttcactgattttttaatttgtttatgggaaattctttaatttttttgatt
[>>.................................... maize ubiquitin promoter regulatory ............................>>]
---------|-----------------|-----------------|-----------------|-----------------|-----------------|-----------
      7,600              7,620             7,640             7,660             7,680             7,700 ggaaacattttcttgtttcgagtagataatgccagcctgttaaacgccgtcgacgagtctaacggacaccaaccagcgaaccagcagcgtcgcgtcgggccaagcg
cctttgtaaaagaacaaagctcatctattacggtcggacaatttgcggcagctgctcagattgcctgtggttggtcgcttggtcgtcgcagcgcagcccggttcgc
[>>.................................... maize ubiquitin promoter regulatory ............................>>]
---------|-----------------|-----------------|-----------------|-----------------|-----------------|-----------
      7,720              7,740             7,760             7,780             7,800

FIG. 1J
``` atgccgtgcacttgtttgtcgggtcatcttttcatgcttttttttgtcttggttgtgatgatgtggtctggttgggcggtcgttctagatcggagtagaattctgtt
tacggcacgtgaacaaacagcccagtagaaaagtacgaaaaaaaacagaaccaacactactacaccagaccaacccgccagcaagatctagcctcatcttaagacaa ubi1; maize ubiquitin intron
Ubi1 5'UTR
Maize Ubi intron
maize ubiquitin promoter regulatory
Maize Ubi gene 8,460  8,480  8,500  8,520  8,540  8,560 tcaaactacctggtggatttattaattttggatctgtatgtgtgtgccatacatattcatagttacgaattgaagatgatggatggaaatatcgatctaggataggt
agtttgatggaccacctaaataattaaaacctagacatacacacacggtatgtataagtatcaatgcttaacttctactacctacctttatagctagatcctatcca ubi1; maize ubiquitin intron
Ubi1 5'UTR
Maize Ubi intron
maize ubiquitin promoter regulatory
Maize Ubi gene 8,580  8,600  8,620  8,640  8,660 atacatgttgatgcgggttttactgatgcatatacagagatgctttttgttcgcttggttgtgatgatgtggtgtggttgggcggtcgttcattcgttctagatcgg
tatgtacaactacgcccaaaatgactacgtatatgtctctacgaaaaacaagcgaaccaacactactacaccacaccaacccgccagcaagtaagcaagatctagcc ubi1; maize ubiquitin intron
Ubi1 5'UTR
Maize Ubi intron
maize ubiquitin promoter regulatory
Maize Ubi gene 8,680  8,700  8,720  8,740  8,760 agtagaatactgtttcaaactacctggtgtatttattaattttggaactgtatgtgtgtgtcatacatcttcatagttacgagtttaagatggatggaaatatcgat
tcatcttatgacaaagtttgatggaccacataaataattaaaaccttgacatacacacacagtatgtagaagtatcaatgctcaaattctacctacctttatagcta ubi1; maize ubiquitin intron
Ubi1 5'UTR
Maize Ubi intron
maize ubiquitin promoter regulatory
Maize Ubi gene 8,780  8,800  8,820  8,840  8,860  8,880 ctaggataggtatacatgttgatgtgggttttactgatgcatatacatgatggcatatgcagcatctattcatatgctctaaccttgagtacctatctattataata
gatcctatccatatgtacaactacacccaaaatgactacgtatatgtactaccgtatacgtcgtagataagtatacgagattggaactcatggatagataatattat ubi1; maize ubiquitin intron
Ubi1 5'UTR
Maize Ubi intron
maize ubiquitin promoter regulatory
Maize Ubi gene 8,900  8,920  8,940  8,960  8,980

FIG. 1L aacaagtatgttttataattattttgatcttgatatacttggatgatggcatatgcagcagctatatgtggattttttagccctgccttcatacgctatttatttg
ttgttcatacaaaatattaataaaactagaactatatgaacctactaccgtatacgtcgtcgatatacacctaaaaaaatcgggacggaagtatgcgataaataaac ubi1; maize ubiquitin intron
Ubi1 "UTR
Maize Ubi intron
maize ubiquitin promoter regulatory
Maize Ubi gene 9,000      9,020      9,040      9,060      9,080 cttggtactgtttcttttgtcgatgctcaccctgttgtttggtgttacttctgcaggtcgactctagaggatccacacgacaccatgtccgcccgcgaggtgcacat
gaaccatgacaaagaaaacagctacgagtgggacaacaaaccacaatgaagacgtccagctgagatctcctaggtgtgctgtggtacaggcgggcgctccacgtgta ubi1; maize ubiquitin intron
Ubi1 "UTR
Maize Ubi intron
maize ubiquitin promoter regulatory
Maize Ubi gene     Omega    tory    cry3 Ab1 protein 9,100      9,120      9,140      9,160      9,180      9,200 cgacgtgaacaacaagaccggccacaccctccagctggaggacaagaccaagctcgacgcggcaggtggcgcacctccccgaccaacgtggccaacgaccagatca
gctgcacttgttgttctggccggtgtgggaggtcgacctcctgttctggttcgagctgccgccgtccaccgcgtggaggggctggttgcaccggttgctggtctagt cry3 Ab1 protein 9,220      9,240      9,260      9,280      9,300 agaccttcgtggccgaatccaacggcttcatgaccggcaccgagggcaccatctactactcaattaatggcgaggccgagatcagcctctacttcgacaacccgttc
tctggaagcaccggcttaggttgccgaagtactggccgtggctcccgtggtagatgatgagttaattaccgctccggctcagtcggagatgaagctgttgggcaag cry3 Ab1 protein 9,320      9,340      9,360      9,380      9,400

PasI
gccggctccaacaaatacgacggccactccaacaagtcccagtacgagatcatcaccgagggcggctccggcaaccagtcccacgtgacctacaccatccagaccac
cggccgaggttgtttatgctgccggtgaggttgttcagggtcatgctctagtagtgggtcccgccgaggccgttggtcagggtgcactggatgtggtaggtctggtg cry3 Ab1 protein 9,420      9,440      9,460      9,480      9,500      9,520

PacI
ctcctcccgctacggccacaagtcctgagtcatgagtcatgagtcagttaacctagacttgtccatcttctggattggccaacttaattaatgtatgaaataaaagg
gaggagggcgatgccggtgttcaggactcagtactcagtactcagtcaattggatctgaacaggtagaagacctaaccggttgaattaattacatactttatttcc cry3 Ab1 protein    polylinker?    pinII Terminator 9,540      9,560      9,580      9,600      9,620 atgcacacatagtgacatgctaatcactataatgtgggcatcaaagttgtgtgttatgtgtaattactagttatctgaataaaagagaaagagatcatccatatttc
tacgtgtgtatcactgtacgattagtgatattacacccgtagtttcaacacacaatacacattaatgatcaatagacttatttttctctttctctagtaggtataaag pinII Terminator 9,640      9,660      9,680      9,700      9,720

FIG. 1M

```
ttatcctaaatgaatgtcacgtgtctttataattctttgatgaaccagatgcatttcattaaccaaatccatatacatataaatattaatcatatataattaatatc
aataggatttacttacagtgcacagaaatattaagaaactacttggtctacgtaaagtaattggtttaggtatatgtatatttataattagtatatattaattatag
               pinII Terminator
  9,740         9,760         9,780         9,800         9,820         9,840

NotI
aattgggttagcaaaacaaatctagtctaggtgtgttttgcgaatgcggccgcggaccgaattggggatctgcatgaaagaaactgtcgcactgctgaaccgcacct
ttaacccaatcgttttgtttagatcagatccacacaaaacgcttacgccggcgcctggcttaaccccctagacgtactttctttgacagcgtgacgacttggcgtgga
         pinII Terminator              polylinker           TA Peroxidase Promoter
       9,860         9,880         9,900         9,920         9,940 tgtcactttcatcgaacacgacctgtgcccaagatgacggtgctgcggtctaagtgaggctgaattgccttggacagaagcggactccctacaattagttaggccaa
acagtgaaagtagcttgtgctggacacgggttctactgccacgacgccagattcactccgacttaacggaacctgtcttcgcctgagggatgttaatcaatccggtt
                              TA Peroxidase Promoter
  9,960         9,980         10,000        10,020        10,040 acggtgcatccatgtgtagctccgggctcgggctgtatcgccatctgcaatagcatccatggagctcgttccatgtagttggagatgaaccaatgatcgggcgtgtg
tgccacgtaggtacacatcgaggcccgagcccgacatagcggtagacgttatcgtaggtacctcgagcaaggtacatcaacctctacttggttactagcccgcacac
                              TA Peroxidase Promoter
 10,060        10,080        10,100        10,120        10,140        10,160 gacgtatgttcctgtgtactccgatagtagagtacgtgttagctctttcatggtgcaagtgaaatttgtgttggtttaattacccctacgttagttgcgggacagga
ctgcatacaaggacacatgaggctatcatctcatgcacaatcgagaaagtaccacgttcactttaaacacaaccaaattaatggggatgcaatcaacgccctgtcct
                              TA Peroxidase Promoter
       10,180        10,200        10,220        10,240        10,260 gacacatcatgaatttaaaggcgatgatgtcctctcctgtaatgttattcttttgatgtgatgaatcaaaatgtcatataaaacatttgttgctctttagttaggcc
ctgtgtagtacttaaatttccgctactacaggagaggacattacaataagaaaactacactacttagttttacagtatattttgtaaacaacgagaaatcaatccgg
                              TA Peroxidase Promoter
  10,280        10,300        10,320        10,340        10,360 tgatcgtagaacgaaatgctcgtgtagcggggctacgagcctatgacgcaataacactggtttgccggcccggagtcgcttgacaaaaaaagcatgttaagtttat
actagcatcttgctttacgagcacatcgccccgatgctcggatactgcgttattgtgaccaaacggccgggcctcagcgaactgtttttttttcgtacaattcaaata
                              TA Peroxidase Promoter
       10,400        10,420        10,440        10,460        10,480

BaeI
ttacaattcaaaacctaacatatttatattccctcaaagcaggttcacgatcacacctgtacctaaaaaaaacatgaagaatatattactccattattatgagatgaa
aatgttaagttttggattgtataatataagggagtttcgtccaagtgctagtgtggacatggattttttttgtacttcttatataatgaggtaataatactctactt
                              TA Peroxidase Promoter
             10,500        10,520        10,540        10,560        10,580
```

FIG. 1N

```
                                                                    BstBI
                                                                      |
ccacttggcaagagtggtaagctatataaaaaaatgaacattattacgagatgttatatgccattatattgattcgaagatatatgtttctttctcccacgggcacc
ggtgaaccgttctcaccattcgatatattttttttacttgtaataatgctctacaatatacggtaatataactaagcttctatatacaaagaaagagggtgcccgtgg
────────────────────────────── TA Peroxidase Promoter ──────────────────────────────»
        10,600          10,620          10,640          10,660          10,680          10,700

BstBI
                                          |
taacggatacatgataaggccaaggcagatcacgggaaattattcgaatacatgttacgccctattgccggaaaaaaaatgcagggcaggtgttggccgtagcgatt
attgcctatgtactattccggttccgtctagtgccctttaataagcttatgtacaatgcgggataacggccttttttttacgtcccgtccacaaccggcatcgctaa
────────────────────────────── TA Peroxidase Promoter ──────────────────────────────»
        10,720          10,740          10,760          10,780          10,800

AflIII
         |
taagcacttaagctggaggttgccacacttggatgcaagcgtctgacccttctaaaaaatcggcggctttgtccgtatccgtatccctatccaacatctagctggc
attcgtgaattcgacctccaacggtgtgaacctacgttcgcagactgggaagattttttagccgccgaaacaggcataggcataggggataggttgtagatcgaccg
────────────────────────────── TA Peroxidase Promoter ──────────────────────────────»
        10,820          10,840          10,860          10,880          10,900 cacacgacggggctgggcagatcgtggatgccgggtcgacgtcgatcgtcagccatcatagaccaatcgaccatctgttatggatgcttgctagctagactagtcag
gtgtgctgccccgacccgtctagcacctacggcccagctgcagctagcagtcggtagtatctggttagctggtagacaataccctacgaacgatcgatctgatcagtc
────────────────────────────── TA Peroxidase Promoter ──────────────────────────────»
        10,920          10,940          10,960          10,980          11,000          11,020 acataaaatttggatactttctcccaactgggagacggggactgatgtgcagctgcacgtgagctaaattttccctataaatatgcatgaaatactgcattatctt
tgtattttaaacctatgaaagagggttgaccctctgccctgactacacgtcgacgtgcactcgatttaaaagggatatttatacgtactttatgacgtaatagaa
────────────────────────────── TA Peroxidase Promoter ──────────────────────────────»
        11,040          11,060          11,080          11,100          11,120 gccacagccactgccacagccagataacaagtgcagctggtagcacgcaacgcatagctctggacttgtagctaggtagccaaccggatccacacgacaccatgctc
cggtgtcggtgacggtgtcggtctattgttcacgtcgaccatcgtgcgttgcgtatcgagacctgaacatcgatccatcggttggcctaggtgtgctgtggtacgag
──────────────────────────── TA Peroxidase Promoter ─────────────────▶  ▭»
        11,140          11,160          11,180          11,200          11,220 gacaccaacaaggtgtacgagatcagcaaccacgccaacggcctctacgccgccacctacctctccctcgacgactccggcgtgtccctcatgaacaagaacgacga
ctgtggttgttccacatgctctagtcgttggtgcggttgccggagatgcggcggtggatggagagggagctgctgaggccgcacagggagtacttgttcttgctgct
────────────────────────────── cry35Ab1 protein ──────────────────────────────»
        11,240          11,260          11,280          11,300          11,320          11,340 cgacatcgacgactacaacctcaagtggttcctcttcccgatcgacgacgaccagtacatcatcacctcctacgccgccaacaactgcaaggtgtggaacgtgaaca
gctgtagctgctgatgttggagttcaccaaggagaagggctagctgctgctggtcatgtagtagtggaggatgcggcggttgttgacgttccacaccttgcacttgt
────────────────────────────── cry35Ab1 protein ──────────────────────────────»
        11,360          11,380          11,400          11,420          11,440
```

FIG. 10

```
acgacaagattaatgtgtcaacctactcctccaccaactccatccagaagtggcagatcaaggccaacggctcctcctacgtgatccagtccgacaacggcaaggtg
tgctgttctaattacacagttggatgaggaggtggttgaggtaggtcttcaccgtcagttccggttgccgaggaggatgcactaggtcaggctgttgccgttccac
```
— cry35Ab1 protein —
11,460    11,480    11,500    11,520    11,540

```
ctcaccgccggcaccggccaggccctcggcctcatccgcctcaccgacgagtcctccaacaacccgaaccagcaatggaacctgacgtccgtgcagaccatccagct
gagtggcggccgtggccggtccgggagccggagtaggcggagtggctgctcaggaggttgttgggcttggtcgttaccttggactgcaggcacgtctggtaggtcga
```
— cry35Ab1 protein —
11,560    11,580    11,600    11,620    11,640    11,660

```
cccgcagaagccgatcatcgacaccaagctcaaggactacccgaagtactccccgaccggcaacatcgacaacggcacctccccgcagctcatgggctggaccctcg
gggcgtcttcggctagtagctgtggttcgagttcctgatgggcttcatgaggggctggccgttgtagctgttgccgtggagggggcgtcgagtacccgacctgggagc
```
— cry35Ab1 protein —
11,680    11,700    11,720    11,740    11,760

```
tgccgtgcatcatggtgaacgacccgaacatcgacaagaacacccagatcaagaccacccccgtactacatcctcaagaagtaccagtactggcagagggccgtgggc
acggcacgtagtaccacttgctgggcttgtagctgttcttgtgggtctagttctggtggggcatgatgtaggagttcttcatggtcatgaccgtctcccggcacccg
```
— cry35Ab1 protein —
11,780    11,800    11,820    11,840    11,860

```
tccaacgtcgcgctccgcccgcacgagaagaagtcctacacctacgagtggggcaccgagatcgaccagaagaccaccatcatcaacaccctcggcttccagatcaa
aggttgcagcgcgaggcgggcgtgctcttcttcaggatgtggatgctcacccccgtggctctagctggtcttctggtggtagtagttgtgggagccgaaggtctagtt
```
— cry35Ab1 protein —
11,880    11,900    11,920    11,940    11,960    11,980

```
catcgacagcggcatgaagttcgacatcccggaggtgggcggcggtaccgacgagatcaagacccagctcaacgaggagctcaagatcgagtattcacatgagacga
gtagctgtcgccgtacttcaagctgtagggcctccacccgccgccatggctgctctagttctgggtcgagttgctcctcgagttctagctcataagtgtactctgct
```
— cry35Ab1 protein —
12,000    12,020    12,040    12,060    12,080

```
agatcatggagaagtaccaggagcagtccgagatcgacaacccgaccgaccagtccatgaactccatcggcttcctcaccatcacctccctggagctctaccgctac
tctagtacctcttcatggtcctcgtcaggctctagctgttgggctggctggtcaggtacttgaggtagccgaaggagtggtagtggagggacctcgagatggcgatg
```
— cry35Ab1 protein —
12,100    12,120    12,140    12,160    12,180

BstAPI

```
aacggctccgagatccgcatcatgcagatccagacctccgacaacgacacctacaacgtgacctcctacccgaaccaccagcaggcc↓tgctgctgctgaccaacca
ttgccgaggctctaggcgtagtacgtctaggtctggaggctgttgctgtggatgttgcactggaggatgggcttggtggtcgtccgggacgacgacgactggttggt
```
— cry35Ab1 protein —
12,200    12,220    12,240    12,260    12,280    12,300

FIG. 1P ctcctacgaggaggtggaggagatcaccaacatcccgaagtccaccctcaagaagctcaagaagtactacttctgagtcatgagtcatgagtcagttaacctagact
gaggatgctcctccacctcctctagtggttgtagggcttcaggtgggagttcttcgagttcttcatgatgaagactcagtactcagtactcagtcaattggatctga cry35Ab1 protein | polylinker 12,320   12,340   12,360   12,380   12,400

PacI tgtccatcttctggattggccaacttaattaatgtatgaaataaaaggatgcacacatagtgacatgctaatcactataatgtgggcatcaaagttgtgtgttatgt
acaggtagaagacctaaccggttgaattaattacatactttattttcctacgtgtgtatcactgtacgattagtgatattacacccgtagtttcaacacacaataca pinII ter 12,420   12,440   12,460   12,480   12,500 gtaattactagttatctgaataaaagagaaagagatcatccatatttcttatcctaaatgaatgtcacgtgtctttataattctttgatgaaccagatgcatttcat
cattaatgatcaatagacttattttctctttctctagtaggtataaagaataggatttacttacagtgcacagaaatattaagaaactacttggtctacgtaaagta pinII ter 12,540   12,560   12,580   12,600   12,620 taaccaaatccatatacatataaatattaatcatatataattaatatcaattgggttagcaaaacaaatctagtctaggtgtgttttgcgaattatcgatgggcccc
attggtttaggtatatgtatatttataattagtatatattaattatagttaacccaatcgttttgtttagatcagatccacacaaaacgcttaatagctacccgggg pinII ter | poly...ker 12,640   12,660   12,680   12,700   12,720

PsrI ggccgaagctggccgcggaccgaattcccatggagtcaaagattcaaatagaggacctaacagaactcgccgtaaagactggcgaacagttcatacagagtctctta
ccggcttcgaccggcgcctggcttaagggtacctcagtttctaagttatctcctggattgtcttgagcggcatttctgaccgcttgtcaagtatgtctcagagaat polylinker | 35s pro 12,740   12,760   12,780   12,800   12,820   12,840 cgactcaatgacaagaagaaaatcttcgtcaacatggtggagcacgacacgcttgtctactccaaaaatatcaaagatacagtctcagaagaccaaagggcaattga
gctgagttactgttcttcttttagaagcagttgtaccacctcgtgctgtgcgaacagatgaggttttttatagtttctatgtcagagtcttctggtttcccgttaact 35s pro 12,860   12,880   12,900   12,920   12,940 gacttttcaacaaagggtaatatccggaaacctcctcggattccattgcccagctatctgtcactttattgtgaagatagtggaaaaggaaggtggctcctacaaat
ctgaaaagttgtttcccattataggccttttggaggagcctaaggtaacgggtcgatagacagtgaaataacacttctatcaccttttccttccaccgaggatgttta 35s pro 12,960   12,980   13,000   13,020   13,040

PshAI gccatcattgcgataaaggaaaggccatcgttgaagatgcctctgccgacagtggtcccaaagatggaccccacccacgaggagcatcgtggaaaaagaagacgtt
cggtagtaacgctatttccttccggtagcaacttctacggagacggctgtcaccagggtttctacctgggggtgggtgctcctcgtagcacctttttcttctgcaa 35s pro 13,060   13,080   13,100   13,120   13,140   13,160

FIG. 1Q

```
ccaaccacgtcttcaaagcaagtggattgatgtgatatctccactgacgtaagggatgacgcacaatcccactatccttcgcaagacccttcctctatataaggaag
ggttggtgcagaagtttcgttcacctaactacactatagaggtgactgcattccctactgcgtgttagggtgataggaagcgttctgggaaggagatatattccttc
```
35s pro 13,180   13,200   13,220   13,240   13,260

```
ttcatttcatttggagaggacagggtacccggggatccaccatgtctccggagaggagaccagttgagattaggccagctacagcagctgatatggccgcggtttgt
aagtaaagtaaacctctcctgtcccatgggccctaggtggtacagaggcctctcctctggtcaactctaatccggtcgatgtcgtcgactataccggcgccaaaca
```
35s pro → | pat protein 13,280   13,300   13,320   13,340   13,360

AleI
```
gatatcgttaaccattacattgagacgtctacagtgaactttaggacagagccacaaacaccacaagagtggattgatgatctagagaggttgcaagatagataccc
ctatagcaattggtaatgtaactctgcagatgtcacttgaaatcctgtctcggtgtttgtggtgttctcacctaactactagatctctccaacgttctatctatggg
```
pat protein 13,380   13,400   13,420   13,440   13,460   13,480

BbvCI
```
ttggttggttgctgaggttgagggtgttgtggctggtattgcttacgctgggccctggaaggctaggaacgcttacgattggacagttgagagtactgtttacgtgt
aaccaaccaacgactccaactcccacaacaccgaccataacgaatgcgacccgggaccttccgatccttgcgaatgctaacctgtcaactctcatgacaaatgcaca
```
pat protein 13,500   13,520   13,540   13,560   13,580

AvrII        AfIII
```
cacataggcatcaaaggttgggcctaggatccacattgtacacacatttgcttaagtctatggaggcgcaaggttttaagtctgtggttgctgttataggccttcca
gtgtatccgtagtttccaacccggatcctaggtgtaacatgtgtgtaaacgaattcagatacctccgcgttccaaaattcagacaccaacgacaatatccggaaggt
```
pat protein 13,600   13,620   13,640   13,660   13,680

```
aacgatccatctgttaggttgcatgaggctttgggatacacagcccggggtacattgcgcgcagctggatacaagcatggtggatggcatgatgttggttttttggca
ttgctaggtagacaatccaacgtactccgaaaccctatgtgtcgggccccatgtaacgcgcgtcgacctatgttcgtaccacctaccgtactacaaccaaaaaccgt
```
pat protein 13,700   13,720   13,740   13,760   13,780   13,800

SbfI
```
aagggattttgagttgccagctcctccaaggccagttaggccagttacccagatctgagtcgacctgcaggcatgcccgctgaaatcaccagtctctctctacaaat
ttccctaaaactcaacggtcgaggaggttccggtcaatccggtcaatgggtctagactcagctggacgtccgtacgggcgactttagtggtcagagagagatgttta
```
pat protein → | polylinker > | 35sTer 13,820   13,840   13,860   13,880   13,900

FIG. 1R

```
ctatctctctctataataatgtgtgagtagttcccagataagggaattagggttcttatagggtttcgctcatgtgttgagcatataagaaacccttagtatgtatt
gatagagagagatattattacacactcatcaagggtctattcccttaatcccaagaatatcccaaagcgagtacacaactcgtatattctttgggaatcatacataa
```
» ══════════════════════════════════ 35sTer ══════════════════════════════════ »
```
        13,920          13,940          13,960          13,980          14,000
```

```
tgtatttgtaaaatacttctatcaataaaatttctaattcctaaaaccaaaatccagggcgagctcgaattcgagctcgagcccgggtggatcctctagagtcgacc
acataaacattttatgaagatagttattttaaagattaaggattttggttttaggtcccgctcgagcttaagctcgagctcgggcccacctaggagatctcagctgg
```
» ══════════ 35sTer ══════════ › ══════════ polylinker ══════════ »
```
14,020          14,040          14,060          14,080          14,100          14,120
```

AscI
```
tgcagaagcttcggtccggcgcgcctctagttgaagacacgttcatgtcttcatcgtaagaagacactcagtagtcttcggccagaatggcctaactcaaggccatc
acgtcttcgaagccaggccgcgcggagatcaacttctgtgcaagtacagaagtagcattcttctgtgagtcatcagaagccggtcttaccggattgagttccggtag
```
» ══════════════════════════════════ polylinker ══════════════════════════════════ »
```
        14,140          14,160          14,180          14,200          14,220
```

BspQI
            SapI              PmeI
```
gtggcctcttgctcttcaggatgaagagctatgtttaaacgtgcaagcgctactagacaattcagtacattaaaaacgtccgcaatgtgttattaagttgtctaagc
caccggagaacgagaagtcctacttctcgatacaaatttgcacgttcgcgatgatctgttaagtcatgtaattttttgcaggcgttacacaataattcaacagattcg
```
» ══════════ polylinker ══════════ › ══════════ Ti plasmid region ══════════ »
```
14,240          14,260          14,280          14,300          14,320
```

BlpI
```
gtcaatttggaacaagtggctatcgccagatataagaacttcgatccgaaatatcgtttcaaaactagaaaacagcgcggctttggctaagccgcgcactatatagg
cagttaaaccttgttcaccgatagcggtctatattcttgaagctaggctttatagcaaagttttgatcttttgtcgcgccgaaaccgattcggcgcgtgatatatcc
```
»› Junction ›
» › LB T-DNA border › ══════════ 3' flanking region:Chr1:15191929..15194301 ══════════ »
```
14,340          14,360          14,380          14,400          14,420          14,440
```

```
attttgggcacctttttgatggaacgtgaaagcgtactgcgcactagttatttaggttgaaccttggatatacggttctcactgcgccaatgcaaggcttgaaacttg
taaaacccgtggaaaactaccttgcactttcgcatgacgcgtgatcaataaatccaacttggaaccatatgccaagagtgacgcggttacgttccgaactttgaac
```
» ══════════════════════ 3' flanking region:Chr1:15191929..15194301 ══════════════════════ »
```
        14,460          14,480          14,500          14,520          14,540
```

SnaBI
```
gttagtaatacgtactccctccgtttctttttatttgtcgctggatagtgcaattttgcactatcgagcgacaaataaaaagaaacggagggagtatatgattgtca
caatcattatgcatgagggaggcaaagaaaaataaacagcgacctatcacgttaaaacgtgatagctcgctgtttattttttctttgcctccctcatatactaacagt
```
» ══════════════════════ 3' flanking region:Chr1:15191929..15194301 ══════════════════════ »
```
        14,560          14,580          14,600          14,620          14,640
```

FIG. 1S

```
gatgtagatatgtttattttatatatcacatacagatatataaaacagatcacttttttcagatatacagttccaatgtcagccctgatcaccctgtcataaattgcac
ctacatctatacaaataaatatatagtgtatgtctatatattttgtctagtgaaaaagtctatatgtcaaggttacagtcgggactagtgggacagtatttaacgtg
```
3' flanking region:Chr1:15191929..15194301

14,680   14,700   14,720   14,740   14,760

```
gtttctaattgatgttgcttcatggtcgtcatgagaaccttctgaagaaatcgatgaaggttgccaacctttcaaagtttcagaaaccactttgcatgtacactaag
caaagattaactacaacgaagtaccagcagtactcttggaagacttctttagctacttccaacggttggaaagtttcaaagtctttggtgaaacgtacatgtgattc
```
3' flanking region:Chr1:15191929..15194301

14,780   14,800   14,820   14,840   14,860

```
ggctggtttggcagcccaaaaccagccagcgttttcctggtcttttctcccgggagaaagcccatgcatagattgtccctggattatttatctgtgtcctttggcta
ccgaccaaaccgtcgggttttggtcggtcgcaaaaggaccagaaaagagggccctctttcgggtacgtatctaacagggacctaataaatagacacaggaaaccgat
```
3' flanking region:Chr1:15191929..15194301

14,880   14,900   14,920   14,940   14,960   14,980

```
aaaattcgtcccaatttcctgtaggaaactacctcggccttggggaggccaggcgattctccaccgcctcgtctcgtccatccttcgatgctcacgcgtgcctcctcg
ttttaagcagggttaaaggacatcctttgatggagccggaaccctccggtccgctaagaggtggcggagcagagcaggtaggaagctacgagtgcgcacggaggagc
```
3' flanking region:Chr1:15191929..15194301

15,000   15,020   15,040   15,060   15,080

```
gatgctatcctcaggcgattctccgtcgtctcgtctcatccatcctcacgcgcgcctcctccgacgctatccccaggcgattctccaccgtctcgtctcatccatcc
ctacgataggagtccgctaagaggcagcagagcagagtaggtaggagtgcgcgcggaggaggctgcgatagggtccgctaagaggtggcagagcagagtaggtagg
```
3' flanking region:Chr1:15191929..15194301

15,100   15,120   15,140   15,160   15,180

MauBI
```
tcatgtacgcctcgtccgatgctatccccagacgattttccgtcgtctcatctccttcatgctcgcgcgcgcctcctccgacgctatccccaggcgattttctgcc
agtacatgcggagcaggctacgatagggggtctgctaaaaggcagcagagtagaggaagtacgagcgcgcgcggaggaggctgcgatagggggtccgctaaaaagacgg
```
3' flanking region:Chr1:15191929..15194301

15,200   15,220   15,240   15,260   15,280   15,300

MauBI
```
gtctcgtctccttcatgcccgcgcgcgcctcctccgacgctatccccaggcgattttccgccgtctcgtctccttcatgcccgcgcgtgcctcctccgacgctattc
cagagcagaggaagtacgggcgcgcgcggaggaggctgcgatagggtccgctaaaaggcggcagagcagaggaagtacgggcgcgcacggaggaggctgcgataag
```
3' flanking region:Chr1:15191929..15194301

15,320   15,340   15,360   15,380   15,400

```
ccacgagcgcctccgccgccgctatccccagacgattttccgctgtctcgtctccttcatgcccgcgcgccctcctccgacgctatcccacgagcgcctccgccg
ggtgctcgcggaggcggcggcgataggggtctgctaaaaggcgacagagcagaggaagtacgggcgcgcggggaggaggctgcgatagggtgctcgcggaggcggc
```
3' flanking region:Chr1:15191929..15194301

15,420   15,440   15,460   15,480   15,500

FIG. 1T

```
ccgctccaccgtcttccccgccgccatcccctta attcctatagatctggacccgctctactttcgttggcatacttttgcttggtgtgcgcgggctggagtggaa
ggcgaggtggcagaaggggcggcggtaggggaattaaggatatctagacctggggcgagatgaaagcaaccgtatgaaaacgaaccacacgcgcccgacctcacctt
```
```
3' flanking region:Chr1:15191929..15194301
```
15,520     15,540     15,560     15,580     15,600     15,620

```
ggttgcgcattcgatcacggggggagaagtggatcttgggtcttggcaggctagggcggttgccaggacgccgtggtgtgcattcatgggtcctataaatctttatca
ccaacgcgtaagctagtgccccctcttcacctagaacccagaaccgtccgatcccgccaacggtcctgcggcaccacacgtaagtacccaggatatttagaaatagt
```
```
3' flanking region:Chr1:15191929..15194301
```
15,640     15,660     15,680     15,700     15,720

AvrII
```
ttaccgccttaggagctagttgtagttcacacatcatatccttttctgctcgacatcgtctggggatgccctaggtgccctaccgaccctacggcattgtcttgacc
aatggcggaatcctcgatcaacatcaagtgtgtagtataggaaaagacgagctgtagcagaccccctacggggatccacgggatggctgggatgccgtaacagaactgg
```
```
3' flanking region:Chr1:15191929..15194301
```
15,740     15,760     15,780     15,800     15,820

```
tctattagactctatgtcatctagagccttcttgggtggccttttgaccccaaagcgaccctatgatcttaccctaacgaggtctcccttggtggggcaagatccac
agataatctgagatacagtagatctcggaagaacccaccggaaaactggggtttcgctgggatactagaatgggattgctccagagggaaccaccccgttctaggtg
```
```
3' flanking region:Chr1:15191929..15194301
```
15,840     15,860     15,880     15,900     15,920     15,940

```
tttgtccacttaactgaagatctgatcctcatcttgaaatctttaatcccaggtgactctacgtcgtatgtggatgctccgggtaacctgccaacccggatcaccc
aaacaggtgaattgacttctagactaggagtagaactttagaaattagggttccactgagatgcagcatacacctacgaggccattggacggttgggcctagtggg
```
```
3' flanking region:Chr1:15191929..15194301
```
15,960     15,980     16,000     16,020     16,040

```
taagatctctttcctaaggggcgagatctaggttcctacgagaaagaagacgaccctgcaccattgcggtccgtccggtccagagtgcgaacgtccggatgcgacac
attctagagaaaggattccccgctctagatccaaggatgctcttttcttctgctgggacgtggtaacgccaggcaggccaggtctcacgcttgcaggcctacgctgtg
```
```
3' flanking region:Chr1:15191929..15194301
```
16,060     16,080     16,100     16,120     16,140

```
agggaaggagtcgctcctgcagcgaggtcgcagactgtccacacagcctcagaaggcaccgccagacaatacatgtaatacccactctgtaagaaaaacctaaaagg
tcccttcctcagcgaggacgtcgctccagcgtctgacaggtgtgtcggagtcttccgtggcggtctgttatgtacattatgggtgagacattcttttggattttcc
```
```
3' flanking region:Chr1:15191929..15194301
```
16,160     16,180     16,200     16,220     16,240     16,260

```
agaaagtatattcctttatctatatgtgtgttatatttctactcaccatcacatgtgaacatctcacttacacaaataaataattaacaaaagacactcaaataaat
tctttcatataaggaaatagatatacacacaatataaagatgagtggtagtgtacacttgtagagtgaatgtgtttatttattaattgttttctgtgagtttattta
```
```
3' flanking region:Chr1:15191929..15194301
```
16,280     16,300     16,320     16,340     16,360

FIG. 1U tatgcatcatgctcgaccttattttgtgtgcattctgttacaatataaaaataatataaaaaaacatatattaatatcaaaatttggagatttaaccctaatatgcaa
atacgtagtacgagctggaataaaaacacacgtaagacaatgttatatttttattatattttttgtatataattatagttttaaacctctaaattgggattatacgtt 3' flanking region:Chr1:15191929..15194301

16,380　　　16,400　　　16,420　　　16,440　　　16,460 atcggagtttagaggaaagaaagaaaaatgctatacaaaataaaggaataaatatataaataaaggtaaaactattaatactggtatattaatttgaacagttgacc
tagcctcaaatctcctttctttcttttacgatatgttttatttccttatttatatatttatttccatttgataattatgaccatataattaaacttgtcaactgg 3' flanking region:Chr1:15191929..15194301

16,480　　　16,500　　　16,520　　　16,540　　　16,560　　　16,580 taattatgaatatcacaactggtttgaattcaaatatgaaatccaagaatttggaaataggaaaaatggagataagaataaaggaaaagaattcttaactcggatgg
attaatacttatagtgttgaccaaacttaagtttatactttaggttcttaaaccttatccttttacctctattcttatttccttttcttaagaattgagcctacc 3' flanking region:Chr1:15191929..15194301

16,600　　　16,620　　　16,640　　　16,660　　　16,680 gcctgggaaacgaatttcggcccacttcctgtgtccttagctgtgcggctcagtccagtg
cggaccctttgcttaaagccgggtgaaggacacaggaatcgacacgccgagtcaggtcac 3' flanking region:Chr1:15191929..15194301

16,700　16,710　16,720　16,730　16,740　16,750

FIG. 1V ic # INIR6 TRANSGENIC MAIZE

REFERENCE TO SEQUENCE LISTING SUBMITTED ELECTRONICALLY

The sequence listing contained in the file named "10085US1_ST25.txt", which is 103,877 bytes as measured in the Windows operating system, and which was created on Mar. 8, 2021 and electronically filed via EFS-Web on Mar. 8, 2021, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An examples of a selected transgenic corn event which confers lepidopteran and coleopteran insect pest tolerance is the DP-4114 transgenic maize event disclosed in U.S. Pat. No. 8,575,434. DP-4114 transgenic maize plants express a Cry1F protein which can confer resistance to European corn borer (ECB, *Ostrinia nubilalis*) infestations as well as cry34Ab1 and cry35Ab1 proteins which can confer resistance to corn rootworm (CRW; *Diabrotica* sp. Including *Diabrotica virgifera virgifera*) infestations. DP-4114 transgenic maize plants also express a phosphinotricin acetyl transferase (PAT) protein which confers tolerance to the herbicide glufosinate.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus are provided. Transgenic maize plant cells comprising an INIR6 transgenic locus comprising an insertion and/or substitution in a DNA junction polynucleotide of a DP-4114 transgenic locus of DNA comprising a cognate guide RNA recognition site (CgRRS) are provided. In certain embodiments, the DP-4114 transgenic locus is set forth in SEQ ID NO:1, is present in seed deposited at the ATCC under accession No. PTA-11506 is present in progeny thereof, is present in allelic variants thereof, or is present in other variants thereof. INIR6 transgenic maize plant cells, transgenic maize plant seeds, and transgenic maize plants all comprising a transgenic locus set forth in SEQ ID NO: 20 are provided. Transgenic maize plant parts including seeds and transgenic maize plants comprising the maize plant cells are also provided.

Methods for obtaining a bulked population of inbred seed comprising selfing the aforementioned transgenic maize plants and harvesting seed comprising the INIR6 transgenic locus from the selfed maize plant are also provided.

Methods of obtaining hybrid maize seed comprising crossing the aforementioned transgenic maize plants to a second maize plant which is genetically distinct from the first maize plant and harvesting seed comprising the INIR6 transgenic locus from the cross are provided. Methods for obtaining a bulked population of seed comprising selfing a transgenic maize plant of comprising SEQ ID NO: 20 and harvesting transgenic seed comprising the transgenic locus set forth in SEQ ID NO: 20 are provided.

A DNA molecule comprising SEQ ID NO: 2, 3, 8, 9, 10, 19, or 20 is provided. Processed transgenic maize plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a maize plant cell comprising the INIR6 transgenic locus of any one of claims 1 to 3, comprising the step of detecting a DNA molecule comprising SEQ ID NO: 2, 3, 8, 9, 10, 19, or 20 are provided.

Methods of excising the INIR6 transgenic locus from the genome of the aforementioned maize plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

BRIEF DESCRIPTION OF THE DRAWINGS/FIGURES

FIG. 1A-W shows a sequence (SEQ ID NO: 1) of the DP-4114 event transgenic locus including the genomic DNA and 5' and 3' junction sequences flanking the inserted transgenic DNA as well as a diagram of transgene expression cassettes and selectable markers in the transgenic locus.

Figure 2:
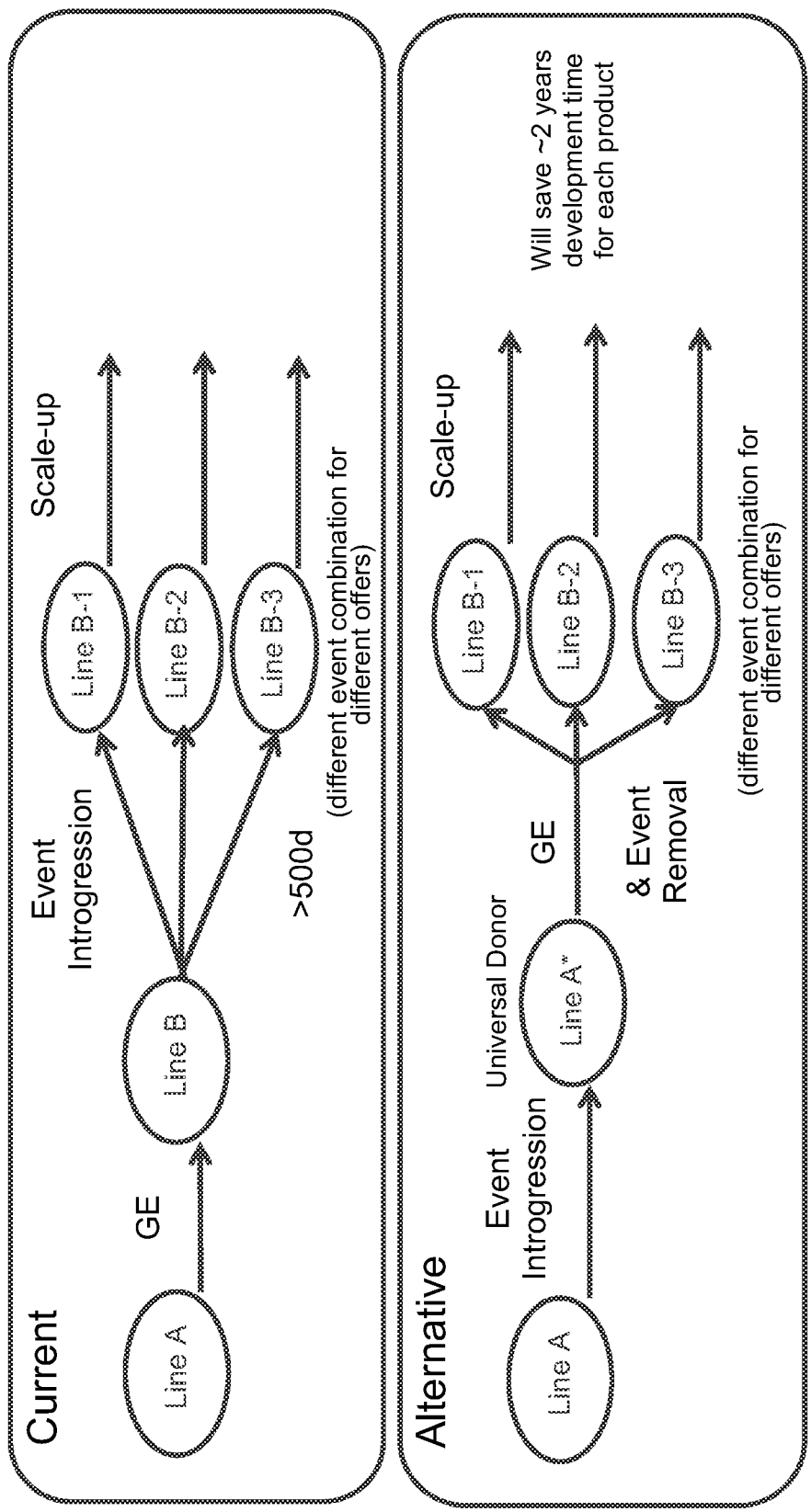

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") with genome editing molecules.

Figure 3A:
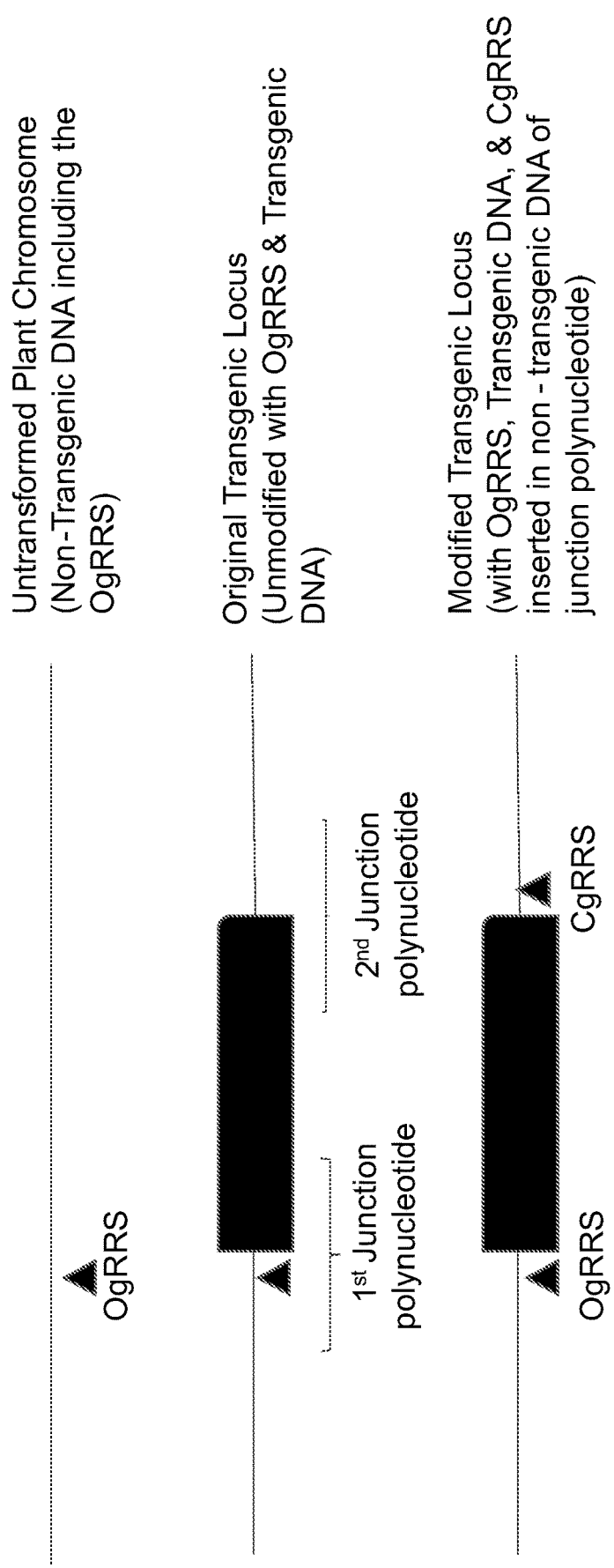
Figure 3B:
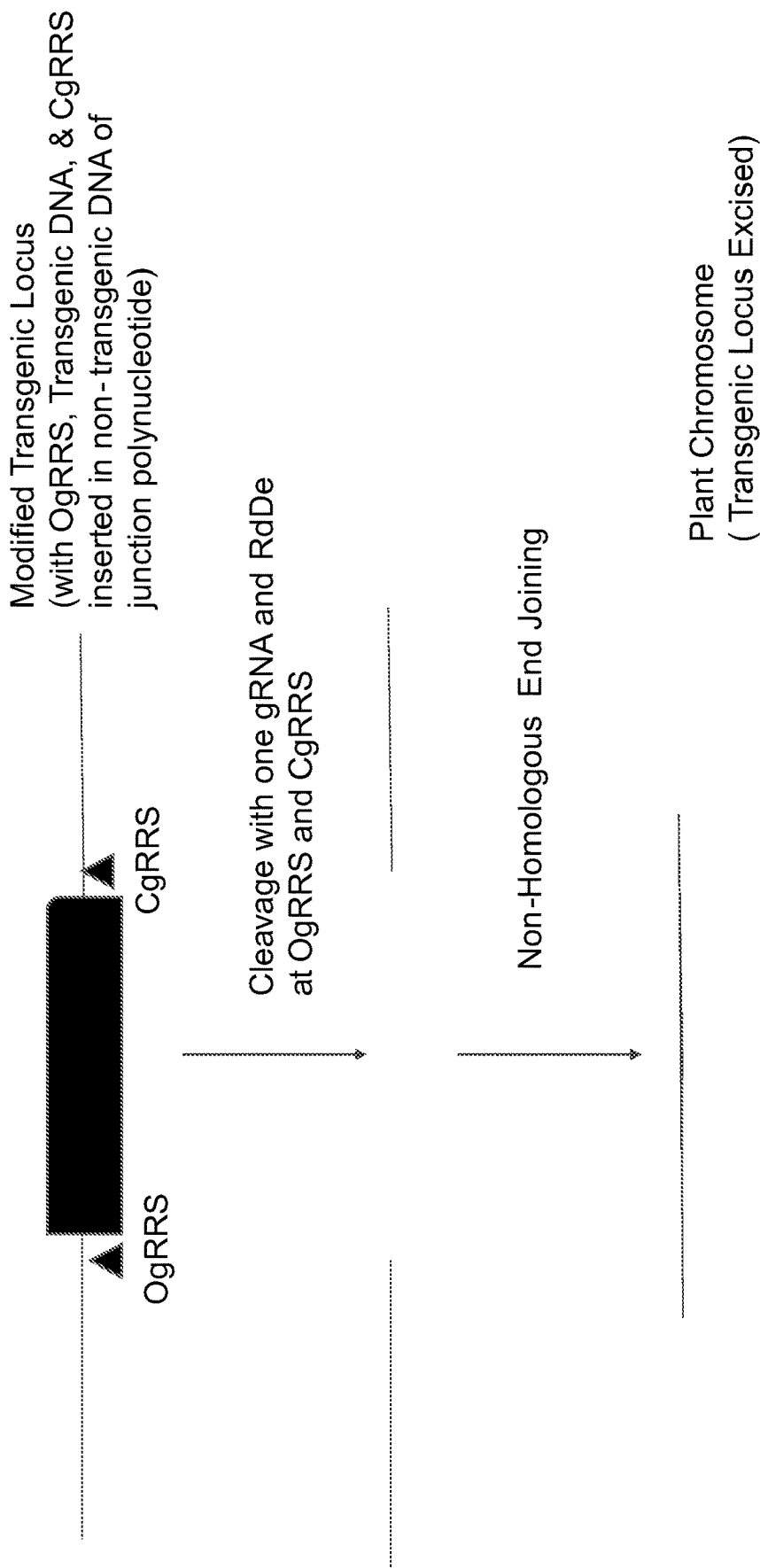

FIG. 3A, B. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the 1$^{st}$ junction polynucleotide (middle); and (iii) the modified transgenic locus with a cognate guide RNA inserted into the non-transgenic DNA of the 2$^{nd}$ junction polynucleotide (bottom). FIG. 3B shows a schematic diagram of a non-limiting example of a process where a modified transgenic locus with a cognate guide RNA inserted into the non-transgenic DNA of the 2$^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 21.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "DP-4114" is used to refer to any of a transgenic maize locus, transgenic maize plants and parts thereof including seed set forth in U.S. Pat. No. 8,575,434, which is incorporated herein by reference in its entirety. Representative DP-4114 transgenic maize seed have been deposited with American Type Culture Collection (ATCC, Manassas, Va. 20110-2209 USA) under Accession No. PTA-11506. DP-4114 transgenic loci include loci having the sequence of SEQ ID NO:1, the sequence of the DP-4114 locus in the deposited seed of Accession No. PTA-11506 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR6" is used to refer either individually collectively to items that include any or all of the DP-4114 transgenic maize loci which have been modified as disclosed herein, modified DP-4114 transgenic maize plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of a targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR6 transgenic loci provided here are characterized by polynucleotide sequences that can facilitate as necessary the removal of the INIR6 transgenic loci from the genome. Useful applications of such INIR6 transgenic loci and related methods of making include targeted excision of a INIR6 transgenic locus or portion thereof in certain breeding lines to facilitate recovery of germplasm with subsets of transgenic traits tailored for specific geographic locations and/or grower preferences. Other useful applications of such INIR6 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR6 transgenic loci or portions thereof which can be selectively excised with one or more gRNA molecules and RdDe (RNA dependent DNA endonucleases) which form gRNA/target DNA complexes. Such selectively excisable INIR6 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 5' junction polynucleotide in an DP-4114 transgenic locus include SEQ ID NO: 7. OgRRS polynucleotide sequences located in a first junction polynucleotide can be introduced into the second junction polynucleotide using donor DNA templates as illustrated in FIG. 3C and as elsewhere described herein. A donor DNA template for introducing the SEQ ID NO: 7 OgRRS into the 3' junction polynucleotide of an DP-4114 locus includes the donor DNA template formed by annealing SEQ ID NO: 11 and 12 or by annealing SEQ ID NO: 11 and 13. Double stranded breaks in a 3' junction polynucleotide of SEQ ID NO: 1 can be introduced with gRNAs encoded by SEQ ID NO: 4, 5, and/or 6 and a Cas12a nuclease. Integration of the SEQ ID NO: 11/12 or 11/13 donor DNA template into the 3' junction polynucleotide of an DP-4114 locus at the double stranded breaks introduced by the gRNAs encoded by SEQ ID NO: 4, 5, and/or 6 and a Cas12a nuclease can provide an INIR6 locus comprising the CgRRS sequence set forth in SEQ ID NO: 8, 9, or 10. Double stranded breaks in a 3' junction polynucleotide of SEQ ID NO: 1 can be introduced with gRNAs encoded by SEQ ID NO: 4, 5, and/or 6. Another donor DNA template adapted for insertion of the OgRRS of SEQ ID NO: 7 in a 3' junction polynucleotide of a DP-4114 transgenic locus can comprise SEQ ID NO: 14. Double stranded breaks in a 3' junction polynucleotide of SEQ ID NO: 1 can be introduced with gRNAs encoded by SEQ ID NO: 5 and a Cas12a nuclease. A donor DNA template of SEQ ID NO: 14 or the equivalent thereof having longer or shorter homology arms can be used to obtain the CgRRS insertion in the 3' junction polynucleotide that is set forth in SEQ ID NO: 19. An INIR6 transgenic locus containing this CgRRS insertion is set forth in SEQ ID NO: 20.

Also provided are unique transgenic locus excision sites created by excision of INIR6 transgenic loci or selectively excisable INIR6 transgenic loci, DNA molecules comprising the INIR6 transgenic loci or unique fragments thereof (i.e., fragments of an INIR6 locus which are not found in an DP-4114 transgenic locus), INIR6 plants comprising the same, biological samples containing the DNA, nucleic acid markers adapted for detecting the DNA molecules, and related methods of identifying maize plants comprising unique INIR6 transgenic locus excision sites and unique fragments of a INIR6 transgenic locus. DNA molecules comprising unique fragments of an INIR6 transgenic locus are diagnostic for the presence of an INIR6 transgenic locus or fragments thereof in a maize plant, maize cell, maize seed, products obtained therefrom (e.g., seed meal or stover), and biological samples.

Figure 1K:
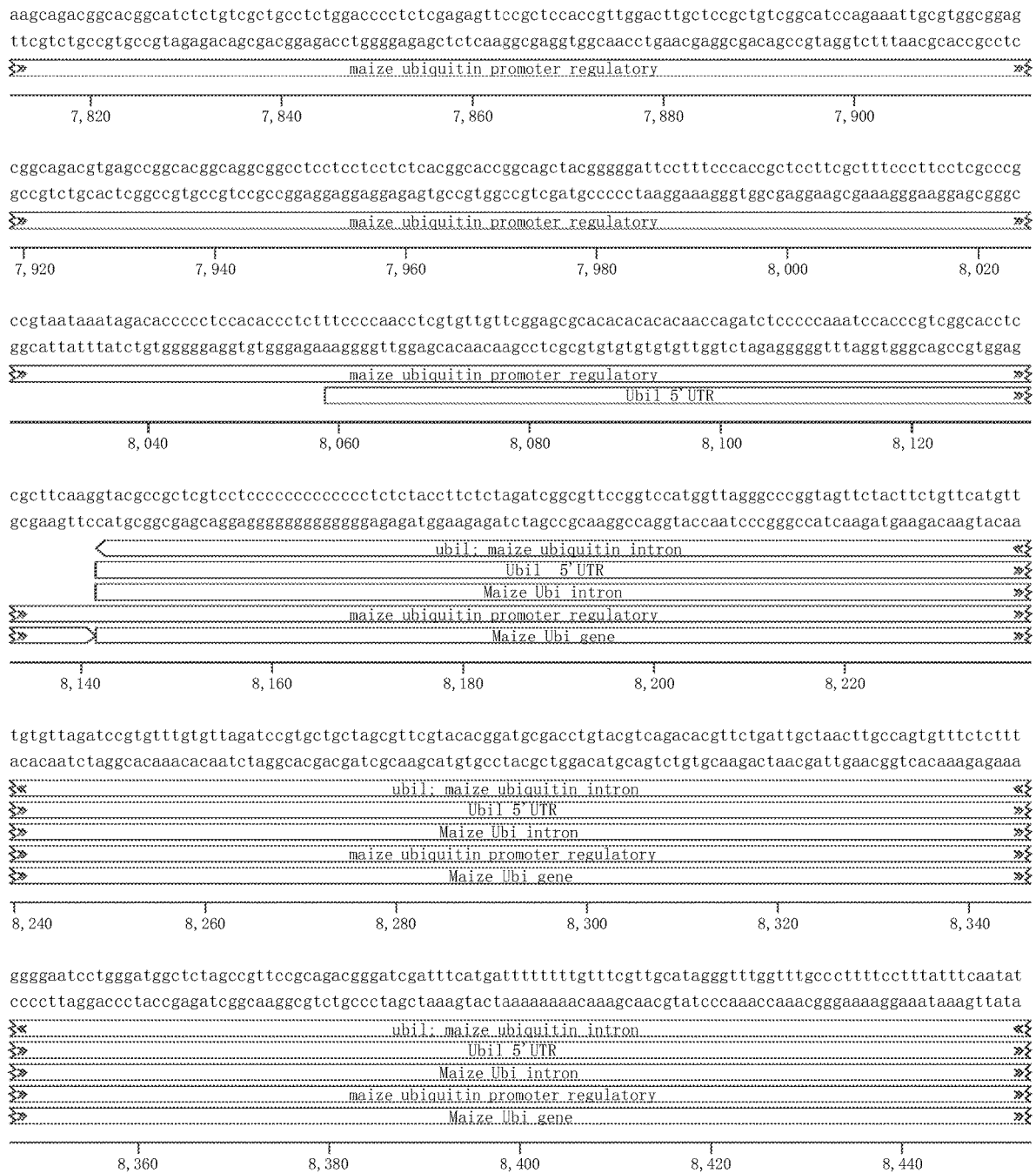
Figure 11B:
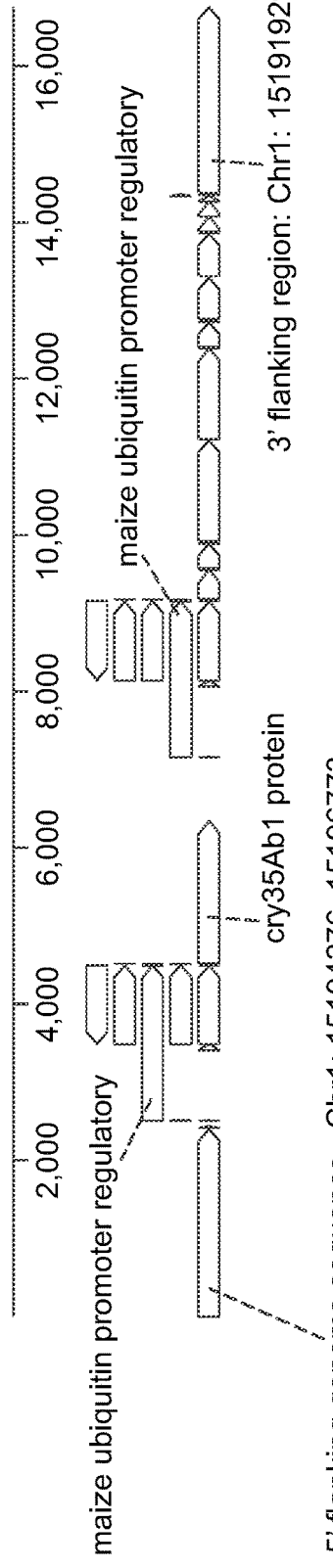

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize DP-4114 transgenic locus. The maize DP-4114 transgenic locus and its transgenic junction sequences are also depicted in FIG. 1. Maize plants comprising the DP-4114 transgenic locus and seed thereof have been cultivated, been placed in commerce, and have been described in a variety of publications by various governmental bodies. Databases which have compiled descriptions of the DP-4114 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the DP-4114 transgenic locus which can be improved by the methods provided herein are set forth or otherwise provided in SEQ ID NO: 1, U.S. Pat. No. 8,575,434, the sequence of the DP-4114 locus in the deposited seed of ATCC accession No. PTA-11506, and elsewhere in this disclosure. In certain embodiments provided herein, the DP-4114 transgenic locus set forth in SEQ ID NO: 1 or present in the deposited seed of ATCC accession No. PTA-11506 is referred to as an "original DP-4114 transgenic locus." Allelic or other variants of the sequence set forth SEQ ID NO: 1, the patent references set forth therein and incorporated herein by reference in their entireties, and elsewhere in this disclosure which may be present in certain variant DP-4114 transgenic plant loci (e.g., progeny of deposited seed of accession No. PTA-11506 which contain allelic variants of SEQ ID NO:1 or progeny originating from transgenic plant cells comprising the original MIR162 transgenic set forth in U.S. Pat. No. 8,575,434) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 10,579 nucleotides of SEQ ID NO: 1. Also provided are plants, plant parts including seeds, genomic DNA, and/or DNA obtained from INIR6 plants which comprise one or more modifications (e.g., via insertion of a CgRRS in a junction polynucleotide sequence) which provide for selective excision of the INIR6 transgenic locus or a portion thereof. Also provided herein are methods of detecting plants, genomic DNA, and/or DNA obtained from plants comprising a INIR6 transgenic locus which contains one or more of a CgRRS, deletions of selectable marker genes, deletions of non-essential DNA, and/or a transgenic locus excision site. A first junction polynucleotide of a DP-4114 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR6 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the DP-4114 transgenic locus of SEQ ID NO: 1, allelic variants thereof, or other variants thereof to obtain an INIR6 transgenic locus. In other embodiments, the OgRRS is found in non-transgenic DNA or transgenic DNA of the 3' junction polynucleotide of the DP-4114 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR6 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR6 transgenic locus, in transgenic DNA of a DNA junction polynucleotide of an INIR6 transgenic locus, or can span the junction of the transgenic and non-transgenic DNA of a DNA junction polynucleotide of an INIR6 transgenic locus. An OgRRS can likewise be located in non-transgenic plant genomic DNA of a DNA junction polynucleotide of an INIR6 transgenic locus, in transgenic DNA of a DNA junction polynucleotide of an INIR6 transgenic locus, or can span the junction of the transgenic and non-transgenic DNA of a DNA junction polynucleotide of an INIR6 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR6 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR6 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize,) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR6 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INIR6 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR6 transgenic loci excision sites are provided herein.

In other embodiments, a segment comprising a INIR6 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and Agrobacterium right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a DP-4114 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR6 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can lack one or more selectable and/or scoreable markers found in an original event (transgenic locus). Original DP-4114 transgenic loci (events), including those set forth in SEQ ID NO: 1), U.S. Pat. No. 8,575,434, the sequence of the DP-4114 locus in the deposited seed of accession No. PTA-11506 and progeny thereof, contain a selectable marker gene encoding a phosphinotricin acetyl transferase (PAT) protein which confers tolerance to the herbicide glufosinate. In certain embodiments provided herein, the DNA element comprising, consisting essentially of, or consisting of the PAT selectable marker gene of an DP-4114 transgenic locus is absent from an INIR6 transgenic locus. The PAT selectable marker cassette can be excised from an original DP-4114 transgenic locus by contacting the transgenic locus with one or more gene editing molecules which introduce double stranded breaks in the transgenic locus at the 5' and 3' end of the expression cassette comprising the PAT selectable marker transgene (e.g., an RdDe and guide RNAs directed to PAM sites located at the 5' and 3' end of the expression cassette comprising the PAT selectable marker transgene) and selecting for plant cells, plant parts, or plants wherein the selectable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable marker transgene by eliminating or reducing promoter activity, introducing a missense mutation, and/or introducing a pre-mature stop codon. In certain embodiments, the selectable PAT marker transgene can be replaced by an introduced transgene. In certain embodiments, an original transgenic locus that was contacted with gene editing molecules which introduce double stranded breaks in the transgenic locus at the 5' and 3' end of the expression cassette comprising the PAT selectable marker transgene can also be contacted with a suitable donor DNA template comprising an expression cassette flanked by DNA homologous to remaining DNA in the transgenic locus located 5' and 3' to the selectable marker excision site. In certain embodiments, a coding region of the PAT selectable marker transgene can be replaced with another coding region such that the replacement coding region is operably linked to the promoter and 3' terminator or polyadenylation site of the PAT selectable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759,618, 7,157,281, 6,852,915, 7,705,216, 10316330, 8618358, 8450561, 8212113, 9428765, 7897748, 8273959, 8093453, 8901378, 9994863, 7928296, and 8466346, each of which are incorporated herein by reference in their entireties.

In certain embodiments, INIR6 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (Streptococcus pyogenes), 5'-NNAGAA (Streptococcus thermophilus CRISPR1), 5'-NGGNG (Streptococcus thermophilus CRISPR3), 5'-NNGRRT or 5'-NNGRR (Staphylococcus aureus Cas9, SaCas9), and 5'-NNNGATT (Neisseria meningitidis). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature,* 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.,* 11:636-646; Mohanta et al. (2017) *Genes* vol. 8,12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.*, 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8,12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 14 and equivalents thereof with longer or shorter homology arms. In certain embodiments, a donor DNA template can comprise an adapter molecule (e.g., a donor DNA template formed by annealing SEQ ID NO: 11 and 12 or by annealing SEQ ID NO: 11 and 13) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

Various treatments are useful in delivery of gene editing molecules and/or other molecules to a DP-4114 or INIR6 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a DP-4114 or INIR6 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the DP-4114 or INIR6 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the DP-4114 or INIR6 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the DP-4114 or INIR6 plant cells in used in the methods provided herein can include dividing cells. Dividing cells can include those cells found in various plant tissues including leaves, meristems, and embryos. These tissues include dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR6 plant from a INIR6 plant cell that had been subjected to the gene editing or from a regenerable plant structure obtained from that INIR6 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR6 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic maize plant cell comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus.

1b. A transgenic maize plant cell comprising an INIR6 transgenic locus comprising an insertion and/or substitution of DNA in a DNA junction polynucleotide of a DP-4114 transgenic locus with DNA comprising a cognate guide RNA recognition site (CgRRS).

2. The transgenic maize plant cell of embodiment 1a or 1b, wherein said CgRRS comprises the DNA molecule set forth in SEQ ID NO: 8, 9, 10, or 19; and/or wherein said DP-4114 transgenic locus is set forth in SEQ ID NO:1, is present in seed deposited at the ATCC under accession No. PTA-11506. is present in progeny thereof, is present in allelic variants thereof, or is present in other variants thereof.

3. The transgenic maize plant cell of embodiments 1a, 1b, or 2, wherein said INIR6 transgenic locus comprises the DNA molecule set forth in SEQ ID NO: 2, 3, or 20.

4. A transgenic maize plant part comprising the maize plant cell of any one of embodiments 1a, 1b, 2, or 3, wherein said maize plant part is optionally a seed.

5. A transgenic maize plant comprising the maize plant cell of any one of embodiments 1a, 1b, 2, or 3.

6. A method for obtaining a bulked population of inbred seed comprising selfing the transgenic maize plant of embodiment 5 and harvesting seed comprising the INIR6 transgenic locus from the selfed maize plant.

7. A method of obtaining hybrid maize seed comprising crossing the transgenic maize plant of embodiment 5 to a second maize plant which is genetically distinct from the first maize plant and harvesting seed comprising the INIR6 transgenic locus from the cross.

8. A DNA molecule comprising SEQ ID NO: 2, 3, 8, 9, 10, 19, or 20.

9. A processed transgenic maize plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a maize plant cell comprising the INIR6 transgenic locus of any one of embodiments 1a, 1b, 2, or 3, comprising the step of detecting DNA molecule comprising SEQ ID NO: 2, 3, 8, 9, 10, 19, or 20.

13. A method of excising the INIR6 transgenic locus from the genome of the maize plant cell of any one of embodiments 1a, 1b, 2, or 3, comprising the steps of:

(a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

EXAMPLES

Example 1. Introduction of a CgRRS in a 3' Junction Polynucleotides of a DP-4114 Transgenic Locus Transgenic plant genomes containing one or more of the following transgenic loci (events) are contacted with:
(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.

Plant cells, callus, parts, or whole plants comprising the introduced CgRRS in the transgenic plant genome are selected.

TABLE 1

Examples of OgRRS and CgRRS in DP-4114

| CORN EVENT NAME | OgRRS | CgRRS |
| --- | --- | --- |
| DP-4114 | tttgtagcacttgcacgtagttacccg (SEQ ID NO: 7; located in 5' junction polynucleotide of SEQ ID NO: 1) | cgcttttgtagcacttgcacgtagttacccgg ata (SEQ ID NO: 8; inserted into 3' junction polynucleotide)<br><br>aacgtgcaagcgcttttgtagcacttgcacg tagttacccggatataagaacttcgatccga aa (SEQ ID NO: 9; inserted into 3' junction polynucleotide)<br>aacgtgcaagcgcttttgtagcacttgcacg tagttacccggccagatataagaacttcgat ccgaaa (SEQ ID NO: 10; inserted into 3' junction polynucleotide) |

Example 2. Insertion of a CgRRS Element in the 3'-Junction of the DP-4114 Event

Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by example. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 14) that targets the 3'-T-DNA junction polynucleotide of the DP-4114 event (SEQ ID NO:1; FIG. 1) for HDR-mediated insertion of a 27 base pair OgRRS sequence (SEQ ID NO: 7) that is identical to a Cas12a recognition site at the 5'-junction polynucleotide of the DP-4114 T-DNA insert is constructed. The DNA donor sequence includes a replacement template with desired insertion region (27 base pairs long) flanked on both sides by homology arms about 500-635 bp in length. The homology arms match (i.e., are homologous to) gDNA (genomic DNA) regions flanking the target gDNA insertion site (SEQ ID NO: 15). The replacement template region comprising the donor DNA is flanked at each end by DNA sequences identical to the DP-4114 3'-T-DNA junction polynucleotide sequence recognized by a Cas12a RNA-guided nuclease and a gRNA (e.g., encoded by SEQ ID NO: 5).

A plant expression cassette that provides for expression of the RNA-guided sequence-specific Cas12a endonuclease is constructed. A plant expression cassette that provides for expression of a guide RNA (e.g., encoded by SEQ ID NO: 5) complementary to sequences adjacent to the insertion site is constructed. An *Agrobacterium* superbinary plasmid transformation vector is constructed. Once the cassettes, donor sequence and *Agrobacterium* superbinary plasmid transformation vector are constructed, they are combined to generate two maize transformation plasmids.

A maize transformation plasmid is constructed with the RNA-guided sequence-specific endonuclease cassette, the guide RNA cassette, and the DP-4114 3'-T_DNA junction sequence DNA donor sequence into the *Agrobacterium* superbinary plasmid transformation vector (the control vector).

A maize transformation plasmid is constructed with the RNA-guided sequence-specific endonuclease cassette, the guide RNA cassette, the SSB cassette, the lambda beta SSAP cassette, the Exo cassette, and the DP-4114 3'-T_DNA junction sequence donor DNA template sequence (SEQ ID NO: 14) into the *Agrobacterium* superbinary plasmid transformation vector (the lambda red vector).

All constructs are transformed into *Agrobacterium* strain LBA4404.

Maize transformations are performed based on published methods.

When a sufficient amount of viable tissue is obtained, it can be screened for insertion at the DP-4114 junction sequence, using a PCR-based approach. The PCR primer on the 5'-end is 5'-tacgctgggccctggaaggctagga-3' (SEQ ID NO: 17). The PCR primer on the 3'-end is 5'-gatggacgagacgaggcggtggaga-3' (SEQ ID NO: 18). The above primers that flank donor DNA homology arms are used to amplify the DP-4114 3'-junction polynucleotide sequence. The correct donor sequence insertion will produce a 1563 bp product. A unique DNA fragment comprising the CgRRS in the DP-4114 3' junction polynucleotide is set forth in SEQ ID NO: 19. Amplicons can be sequenced directly using an amplicon sequencing approach or ligated to a convenient plasmid vector for Sanger sequencing. Those plants in which the DP-4114 junction sequence now contains the intended Cas12a recognition sequence are selected and grown to maturity. The T-DNA encoding the Cas12a reagents can be segregated away from the modified junction sequence in a subsequent generation. The resultant INIR6 transgenic locus (SEQ ID NO: 20) comprising the CgRRS and OgRRS (e.g., which each comprise SEQ ID NO: 7) can be excised using Cas12a and a suitable gRNA which hybridizes to DNA comprising SEQ ID NO: 7 at both the OgRRS and the CgRRS.

The breadth and scope of the present disclosure should not be limited by any of the above-described embodiments.

What is claimed is:

1. A transgenic maize plant cell comprising a transgenic locus comprising the sequence of SEQ ID NO: 20.

2. A transgenic maize plant seed comprising a transgenic locus comprising the sequence of SEQ ID NO: 20.

3. A transgenic maize plant comprising a transgenic locus comprising the sequence of SEQ ID NO: 20.

4. A method for obtaining a bulked population of seed comprising selfing the transgenic maize plant of claim 3 and harvesting transgenic seed comprising the transgenic locus comprising the sequence of SEQ ID NO: 20.

* * * * *

SEQUENCE LISTING

```
<160> NUMBER OF SEQ ID NOS: 21

<210> SEQ ID NO 1
<211> LENGTH: 16752
<212> TYPE: DNA
<213> ORGANISM: Artificial
<220> FEATURE:
<223> OTHER INFORMATION: synthetic

<400> SEQUENCE: 1
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
gatgttgatg attggtctag agctagaggc ctatagccct atactactgt gtattgtccg     240 ccgtttagt tttttggtcc catcccatca atgcaaccgc cttgttttgc tccaattgtc      300
ccgttcctgc gcctcgcttt tgctctgtcg catcgcatac aaaaaaaaaa acgccgcgcc     360
ggctttgaat cgcgccccc aactgctcca accaggcaac ggacacggcc accgtccgtg      420
tcgcgagcaa aaaacaaaa agaggaacgc gtccaggacg aagcagtcca ctgccgctgt      480
ggccggcaaa agatctggtt gagcacatgg agattggaga aggttggttg gttcttctgg     540
aaacgccaat gaatgggggc actgacatgt actcttaaca tgtagtgcaa tccagagatc     600
ggatatccag acactggcag cacgatcgcc tcgcgccgta gatcacgcac gcaaattact     660
gaagaccatt cacaaaaaaa aaaaaacaca caggggctag cgtgccccac accaaaccca     720
agtgctgcgt tgcacgcagg ggagcgaaaa aaaacaataa tgctcactgt cacgtcgcgt     780
atccaacccc gcggacgtct cggctctcag cagcagcaca cggggcacct cacgatgccg     840
ttctcgttgc actccgtgca ccgccggaac ccgccgccgc attcgtcgcc ctcctcctcc     900
tcctccgcct cgtcttcgtc acccacgtac accttgcagc tgcccgagca gacatcgcag     960
agcacgaacc gcatgtcccc gcaggcctcg cacgcgccgg cgtcgccgcc gtgtgggccg    1020
gccgtcgacg cagcgctctc gcacccgcc agcctcggcg cgagctcccc ggcctcgtgc     1080
agccgcttca gctcctcggc gttgcccacg agctcccccgt ccacgaagag gctgggagg    1140
```

```
gcggcgggcg tgccgccggc ttggccgagc ccgaggccga aaggccgcg  gagctcgtcc   1200 cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtggacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaagaaca agaagagtat    2040 ttggagctac tgaacattct cttttcctga agataactaa ttttggaac attcagactt    2100 gggagtctgg acttttggag ggaagttcaa attgtggtct gcctctgcca tgtgttgttt   2160
tttagtcgga gagtggccct cattttttt gtcctgttta gctttatagt cgtagcagct    2220
agtagcgaaa tttaaccttg gattatggcc gtgttagtca aacaatcatt gatttatttc   2280 ctcccctttcg cgctgctttt cctgtacgca tctccgctgc ccttgattcg aggaccctgt   2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta   2460
cccggaccga agcttcggcc ggggcccatc gatatccgcg ggcatgcctg cagtgcagcg   2520
tgacccggtc gtgcccctct ctagagataa tgagcattgc atgtctaagt tataaaaaat   2580
taccacatat ttttttgtc acacttgttt gaagtgcagt ttatctatct ttatacatat    2640
atttaaactt tactctacga ataatataat ctatagtact acaataatat cagtgtttta   2700
gagaatcata taaatgaaca gttagacatg gtctaaagga caattgagta tttttgacaac  2760 aggactctac agtttatct ttttagtgtg catgtgttct cctttttttt tgcaaatagc    2820
ttcacctata taatacttca tccattttat tagtacatcc atttagggtt tagggttaat   2880 ggttttata gactaatttt tttagtacat ctattttatt ctattttagc ctctaaatta    2940
agaaaactaa aactctattt tagttttttt atttaataat ttagatataa aatagaataa   3000
aataaagtga ctaaaaatta aacaaatacc ctttaagaaa ttaaaaaaac taaggaaaca   3060
tttttcttgt ttcgagtaga taatgccagc ctgttaaacg ccgtcgacga gtctaacgga   3120
caccaaccag cgaaccagca gcgtcgcgtc gggccaagcg aagcagacgg cacggcatct   3180
ctgtcgctgc ctctgacccc ctctcgagag ttccgctcca ccgttggact tgctccgctg   3240
tcggcatcca gaaattgcgt ggcggagcgg cagacgtgag ccggcacggc aggcggcctc   3300
ctcctcctct cacggcaccg gcagctacgg gggattcctt tcccaccgct ccttcgcttt   3360
cccttcctcg cccgccgtaa taatagaca ccccctccac accctctttc cccaacctcg    3420
tgttgttcgg agcgcacaca cacacaacca gatctcccc  aaatccaccc gtcggcacct   3480
```

```
ccgcttcaag gtacgccgct cgtcctcccc cccccccccct ctctaccttc tctagatcgg   3540
cgttccggtc catggttagg gcccggtagt tctacttctg ttcatgtttg tgttagatcc   3600
gtgtttgtgt tagatccgtg ctgctagcgt tcgtacacgg atgcgacctg tacgtcagac   3660
acgttctgat tgctaacttg ccagtgtttc tctttgggga atcctgggat ggctctagcc   3720
gttccgcaga cgggatcgat ttcatgattt ttttgtttc gttgcatagg gtttggtttg   3780
cccttttcct ttatttcaat atatgccgtg cacttgtttg tcgggtcatc ttttcatgct   3840 ttttttgtc ttggttgtga tgatgtggtc tggttgggcg gtcgttctag atcggagtag   3900
aattctgttt caaactacct ggtggattta ttaattttgg atctgtatgt gtgtgccata   3960
catattcata gttacgaatt gaagatgatg gatggaaata tcgatctagg ataggtatac   4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aattttggaa ctgtatgtgt gtgtcataca tcttcatagt   4200
tacgagttta agatggatgg aaatatcgat ctaggatagg tatacatgtt gatgtgggtt   4260
ttactgatgc atatacatga tggcatatgc agcatctatt catatgctct aaccttgagt   4320
acctatctat tataataaac aagtatgttt tataattatt ttgatcttga tatacttgga   4380
tgatggcata tgcagcagct atatgtggat tttttagcc ctgccttcat acgctattta   4440
tttgcttggt actgtttctt ttgtcgatgc tcaccctgtt gtttggtgtt acttctgcag   4500
gtcgactcta gaggatccaa caatggagaa caacatacag aatcagtgcg tccctacaa   4560 ctgcctcaac aatcctgaag tagagattct caacgaagag aggtcgactg gcagattgcc   4620
gttagacatc tccctgtccc ttacacgttt cctgttgtct gagtttgttc caggtgtggg   4680
agttgcgttt ggcctcttcg acctcatctg gggcttcatc actccatctg attggagcct   4740 cttctcttctc cagattgaac agttgattga acaaaggatt gagaccttgg aaaggaatcg   4800
ggccatcact acccttcgtg gcttagcaga cagctatgag atctacattg aagcactaag   4860
agagtgggaa gccaatccta acaatgccca actgagagaa gatgtgcgta tacgctttgc   4920
taacacagat gatgctttga tcacagccat caacaacttc acccttacca gcttcgagat   4980
ccctcttctc tcggtctatg ttcaagctgc taacctgcac ttgtcactac tgcgcgacgc   5040
tgtgtcgttt gggcaaggtt ggggactgga catagctact gtcaacaatc actacaacag   5100
actcatcaat ctgattcatc gatacacgaa acattgtttg gatacctaca atcagggatt   5160
ggagaacctg agaggtacta acactcgcca atgggccagg ttcaatcagt tcaggagaga   5220
ccttacactt actgtgttag acatagttgc tctctttccg aactacgatg ttcgtaccta   5280
tccgattcaa acgtcatccc aacttacaag ggagatctac accagttcag tcattgaaga   5340
ctctccagtt tctgcgaaca tacccaatgg tttcaacagg gctgagtttg gagtcagacc   5400
accccatctc atggacttca tgaactcttt gtttgtgact gcagagactg ttagatccca   5460
aactgtgtgg ggaggacact tagttagctc acgcaacacg gctggcaatc gtatcaactt   5520
tcctagttac ggggtcttca atcccggggg cgccatctgg attgcagatg aagatccacg   5580 tccttttctat cggaccttgt cagatcctgt cttcgtccga ggaggctttg gcaatcctca   5640
ctatgtactc ggtcttaggg gagtggcctt tcaacaaact ggtacgaatc acccgcac   5700 attcaggaac tccgggacca ttgactctct agatgagata ccacctcaag acaacagcgg   5760
cgcaccttgg aatgactact cccatgtgct gaatcatgtt acctttgtgc gctggccagg   5820
tgagatctca ggttccgact catggagagc accaatgttc tcttggacgc atcgtagcgc   5880
```

```
tacccccaca aacaccattg atccagagag aatcactcag attcccttgg tgaaggcaca    5940
cacacttcag tcaggaacta cagttgtaag agggccgggg ttcacgggag agacattct     6000
tcgacgcact agtggaggac cattcgcgta caccattgtc aacatcaatg gcaacttcc     6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgcccccggt tcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgtttga ttgagatatc atcaatatta taataaaaat     6720
atccattaaa cacgatttga tacaaatgac agtcaataat ctgatttgaa tatttattaa    6780
ttgtaacgaa ttcataaag atcgaataga aaatactgca ctgcaaatga aaattaacac     6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccgt cgtgccctc tctagagata     7200
atgagcattg catgtctaag ttataaaaaa ttaccacata tttttttgt cacacttgtt     7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc tttttagtgt    7440
gcatgtgttc tccttttttt ttgcaaatag cttcacctat ataatacttc atccatttta    7500
ttagtacatc catttagggt ttagggttaa tggttttat agactaattt ttttagtaca     7560
tctattttat tctattttag cctctaaatt aagaaaacta aaactctatt ttagttttt     7620
tatttaataa tttagatata aaatagaata aataaagtg actaaaaatt aaacaaatac     7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
```

```
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gcccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc tccagctgg    9240 aggacaagac caagctcgac ggcggcaggt ggcgcacctc cccgaccaac gtggccaacg    9300
accagatcaa gaccttcgtg gccgaatcca acggcttcat gaccggcacc gagggccacc    9360
tctactactc aattaatggc gaggccgaga tcagcctcta cttcgacaac ccgttcgccg    9420
gctccaacaa atacgacggc cactccaaca gtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtgagtac   10200 gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaacatttt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
```

```
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaat gcagggcagg tgttggccgt    10800
agcgatttaa gcacttaagc tggaggttgc cacacttgga tgcaagcgtc tgacccttct   10860
aaaaaatcgg cggctttgtc cgtatccgta tccctatcc aacatctagc tggccacacg    10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacacccte ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc    12180
ctggagctct accgctacaa cggctccgag atccgcatca tgcagatcca gacctccgac   12240
aacgacacct caacgtgac ctcctacccg aaccaccagc aggccctgct gctgctgacc    12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg ccaacttaa ttaatgtatg aaataaaagg atgcacacat agtgacatgc    12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccggccgaa gctggccgcg gaccgaattc ccatggagtc aaagattcaa   12780
atagaggacc taacagaact cgccgtaaag actggcgaac agttcataca gagtctctta   12840
cgactcaatg acaagaagaa aatcttcgtc aacatggtgg agcacgacac gcttgtctac   12900
tccaaaaata tcaaagatac agtctcagaa gaccaaaggg caattgagac ttttcaacaa   12960
```

```
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg acccccacc cacgaggagc    13140 atcgtggaaa aagaagacgt tccaaccacg tcttcaaagc aagtggattg atgtgatatc   13200
tccactgacg taagggatga cgcacaatcc cactatcctt cgcaagaccc ttcctctata   13260
taaggaagtt catttcattt ggagaggaca gggtacccgg ggatccacca tgtctccgga   13320
gaggagacca gttgagatta ggccagctac agcagctgat atggccgcgg tttgtgatat   13380
cgttaaccat tacattgaga cgtctacagt gaactttagg acagagccac aaacaccaca   13440
agagtggatt gatgatctag agaggttgca agatagatac ccttggttgg ttgctgaggt   13500
tgagggtgtt gtggctggta ttgcttacgc tgggccctgg aaggctagga acgcttacga   13560
ttggacagtt gagagtactg tttacgtgtc acataggcat caaaggttgg gcctaggatc   13620
cacattgtac acacatttgc ttaagtctat ggaggcgcaa ggttttaagt ctgtggttgc   13680
tgttataggc cttccaaacg atccatctgt taggttgcat gaggctttgg gatacacagc   13740
ccggggtaca ttgcgcgcag ctggatacaa gcatggtgga tggcatgatg ttggttttg    13800 gcaaagggat tttgagttgc cagctcctcc aaggccagtt aggccagtta cccagatctg   13860
agtcgacctg caggcatgcc cgctgaaatc accagtctct ctctacaaat ctatctctct   13920
ctataataat gtgtgagtag ttcccagata agggaattag ggttcttata gggtttcgct   13980
catgtgttga gcatataaga aacccttagt atgtatttgt atttgtaaaa tacttctatc   14040
aataaaattt ctaattccta aaaccaaaat ccagggcgag ctcgaattcg agctcgagcc   14100
cgggtggatc ctctagagtc gacctgcaga agcttcggtc cggcgcgcct ctagttgaag   14160
acacgttcat gtcttcatcg taagaagaca ctcagtagtc ttcggccaga atggcctaac   14220
tcaaggccat cgtggcctct tgctcttcag gatgaagagc tatgtttaaa cgtgcaagcg   14280
ctactagaca attcagtaca ttaaaaacgt ccgcaatgtg ttattaagtt gtctaagcgt   14340
caatttggaa caagtggcta tcgccagata taagaacttc gatccgaaat atcgtttcaa   14400
aactagaaaa cagcgcggct ttggctaagc cgcgcactat ataggatttt gggcacctt   14460 tgatggaacg tgaaagcgta ctgcgcacta gttatttagg ttgaaccttg gatatacggt   14520
tctcactgcg ccaatgcaag gcttgaaact tggttagtaa tacgtactcc ctccgtttct   14580
ttttatttgt cgctggatag tgcaatttg cactatcgag cgacaaataa aaagaaacgg    14640
agggagtata tgattgtcag atgtagatat gtttatttat atatcacata cagatatata   14700
aaacagatca cttttcaga tatacagttc caatgtcagc cctgatcacc ctgtcataaa    14760
ttgcacgttt ctaattgatg ttgcttcatg gtcgtcatga gaaccttctg aagaaatcga   14820
tgaaggttgc caacctttca aagtttcaga aaccactttg catgtacact aagggctggt   14880
ttggcagccc aaaaccagcc agcgttttcc tggtcttttc tcccgggaga agcccatgc    14940 atagattgtc cctggattat ttatctgtgt cctttggcta aaaattcgtc ccaatttcct   15000
gtaggaaact acctcggcct tgggaggcca ggcgattctc caccgcctcg tctcgtccat   15060
ccttcgatgc tcacgcgtgc ctcctccgat gctatcctca ggcgattctc cgtcgtctcg   15120
tctcatccat cctcacgcgc gcctcctccg acgctatccc caggcgattc tccaccgtct   15180
cgtctcatcc atcctcatgt acgcctcgtc cgatgctatc cccagacgat tttccgtcgt   15240
ctcatctcct tcatgctcgc gcgcgcctcc tccgacgcta tccccaggcg atttttctgc   15300
cgtctcgtct ccttcatgcc cgcgcgcgcc tcctccgacg ctatccccag gcgattttcc   15360
```

```
gccgtctcgt ctccttcatg cccgcgcgtg cctcctccga cgctattccc acgagcgcct   15420
ccgccgccgc tatccccaga cgattttccg ctgtctcgtc tccttcatgc ccgcgcgccc   15480
ctcctccgac gctatcccca cgagcgcctc cgccgccgct ccaccgtctt cccgccgcc    15540 atccccttaa ttcctataga tctgacccc gctctacttt cgttggcata cttttgcttg    15600
gtgtgcgcgg gctggagtgg aaggttgcgc attcgatcac gggggagaag tggatcttgg   15660
gtcttggcag gctagggcgg ttgccaggac gccgtggtgt gcattcatgg gtcctataaa   15720
tctttatcat taccgcctta ggagctagtt gtagttcaca catcatatcc ttttctgctc   15780
gacatcgtct ggggatgccc taggtgccct accgaccta cggcattgtc ttgacctcta    15840
ttagactcta tgtcatctag agccttcttg ggtggccttt tgaccccaaa gcgaccctat   15900
gatcttaccc taacgaggtc tcccttggtg gggcaagatc cactttgtcc acttaactga   15960
agatctgatc ctcatcttga aatctttaat cccaaggtga ctctacgtcg tatgtggatg   16020
ctccgggtaa cctgccaacc cggatcaccc taagatctct ttcctaaggg gcagagatcta  16080 ggttcctacg agaaagaaga cgaccctgca ccattgcggt ccgtccggtc cagagtgcga   16140
acgtccggat gcgacacagg gaaggagtcg ctcctgcagc gaggtcgcag actgtccaca   16200
cagcctcaga aggcaccgcc agacaataca tgtaataccc actctgtaag aaaaacctaa   16260
aaggagaaag tatattcctt tatctatatg tgtgttatat ttctactcac catcacatgt   16320
gaacatctca cttacacaaa taaataatta acaaaagaca ctcaaataaa ttatgcatca   16380
tgctcgacct tattttgtgt gcattctgtt acaatataaa aataatataa aaaacatata   16440
ttaatatcaa aatttggaga tttaacccta atatgcaaat cggagtttag aggaaagaaa   16500
gaaaaatgct atacaaaata aaggaataaa tatataaata aaggtaaaac tattaatact   16560
ggtatattaa tttgaacagt tgacctaatt atgaatatca caactggttt gaattcaaat   16620
atgaaatcca agaatttgga aataggaaaa atggagataa gaataaagga aaagaattct   16680
taactcggat gggcctggga aacgaatttc ggcccacttc ctgtgtcctt agctgtgcgg   16740
ctcagtccag tg                                                      16752
```

<210> SEQ ID NO 2
<211> LENGTH: 16695
<212> TYPE: DNA
<213> ORGANISM: Artificial
<220> FEATURE:
<223> OTHER INFORMATION: synthetic

<400> SEQUENCE: 2

```
gagcatatcc agcaccagct ggtaccaagg tcgggtctct gtgctagtgc tattagctag     60
tgtaaggagc gagtaggtca gttaaggctg gtgcgtcgtg agggctgtct tgtgtgtagc    120
tacagcagac ggttcatcag aaggattatt cgtgcagtat atacagtaca actagacaat    180
gatgttgatg attggtctag agctagaggc ctatagccct atactactgt gtattgtccg    240
ccgttttagt ttttggtcc catcccatca atgcaaccgc cttgttttgc tccaattgtc     300
ccgttcctgc gcctcgcttt tgctctgtcg catcgcatac aaaaaaaaaa acgccgcgcc    360
ggctttgaat cgcgcccccc aactgctcca accaggcaac ggacacggcc accgtccgtg    420
tcgcgagcaa aaaacaaaa agaggaacgc gtccaggacg aagcagtcca ctgccgctgt     480
ggccggcaaa agatctggtt gagcacatgg agattggaga aggttggttg gttcttctgg    540
aaacgccaat gaatgggggc actgcacatgt actcttaaca tgtagtgcaa tccagagatc   600
```

-continued

```
ggatatccag acactggcag cacgatcgcc tcgcgccgta gatcacgcac gcaaattact    660
gaagaccatt cacaaaaaaa aaaaaacaca caggggctag cgtgcccac accaaaccca      720 agtgctgcgt tgcacgcagg ggagcgaaaa aaaacaataa tgctcactgt cacgtcgcgt    780
atccaacccc gcggacgtct cggctctcag cagcagcaca cggggcacct cacgatgccg    840
ttctcgttgc actccgtgca ccgccggaac ccgccgccgc attcgtcgcc ctcctcctcc    900
tcctccgcct cgtcttcgtc acccacgtac accttgcagc tgcccgagca gacatcgcag    960
agcacgaacc gcatgtcccc gcaggcctcg cacgcgccgg cgtcgccgcc gtgtgggccg   1020
gccgtcgacg cagcgctctc gcacccggcc agcctcggcg cgagctcccc ggcctcgtgc   1080
agccgcttca gctcctcggc gttgcccacg agctccccgt ccacgaagag gctggggagg   1140
gcggcgggcg tgccgccggc ttggccgagc ccgaggccga aaggccgcg gagctcgtcc    1200 cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttccctccc cgccgctcgt cggggcggcg    1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtggacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttttggaac attcagactt   2100 gggagtctgg acttttggag ggaagttcaa attgtggtct gcctctgcca tgtgttgttt   2160
tttagtcgga gagtggccct cattttttt gtcctgttta gctttatagt cgtagcagct   2220
agtagcgaaa tttaaccttg gattatggcc gtgttagtca aacaatcatt gatttatttc   2280 ctcccttcg cgctgctttt cctgtacgca tctccgctgc ccttgattcg aggaccctgt    2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta   2460
cccggaccga agcttcggcc ggggcccatc gatatccgcg ggcatgcctg cagtgcagcg   2520
tgacccggtc gtgcccctct ctagagataa tgagcattgc atgtctaagt tataaaaaat   2580
taccacatat ttttttgtc acacttgttt gaagtgcagt ttatctatct ttatacatat    2640
atttaaactt tactctacga ataatataat ctatagtact acaataatat cagtgtttta   2700
gagaatcata taaatgaaca gttagacatg gtctaaagga caattgagta ttttgacaac   2760
aggactctac agttttatct ttttagtgtg catgtgttct ccttttttt tgcaaatagc    2820 ttcacctata taatacttca tccatttat tagtacatcc atttagggtt tagggttaat    2880 ggttttata gactaatttt tttagtacat ctatttatt ctatttagc ctctaaatta      2940 agaaaactaa aactctattt tagttttttt atttaataat ttagatataa aatagaataa   3000
```

```
aataaagtga ctaaaaatta aacaaatacc ctttaagaaa ttaaaaaaac taaggaaaca   3060 ttttcttgt ttcgagtaga taatgccagc ctgttaaacg ccgtcgacga gtctaacgga   3120
caccaaccag cgaaccagca gcgtcgcgtc gggccaagcg aagcagacgg cacggcatct   3180
ctgtcgctgc ctctggaccc ctctcgagag ttccgctcca ccgttggact tgctccgctg   3240
tcggcatcca gaaattgcgt ggcggagcgg cagacgtgag ccggcacggc aggcggcctc   3300
ctcctcctct cacggcaccg gcagctacgg gggattcctt tcccaccgct ccttcgcttt   3360
cccttcctcg cccgccgtaa taaatagaca ccccctccac accctctttc cccaacctcg   3420
tgttgttcgg agcgcacaca cacacaacca gatctccccc aaatccaccc gtcggcacct   3480
ccgcttcaag gtacgccgct cgtcctcccc cccccccct ctctaccttc tctagatcgg   3540
cgttccggtc catggttagg gcccggtagt tctacttctg ttcatgtttg tgttagatcc   3600
gtgtttgtgt tagatccgtg ctgctagcgt tcgtacacgg atgcgacctg tacgtcagac   3660
acgttctgat tgctaacttg ccagtgtttc tctttgggga atcctgggat ggctctagcc   3720
gttccgcaga cgggatcgat ttcatgattt ttttgtttc gttgcatagg gtttggtttg   3780
cccttttcct ttatttcaat atatgccgtg cacttgtttg tcgggtcatc ttttcatgct   3840
tttttttgtc ttggttgtga tgatgtggtc tggttgggcg gtcgttctag atcggagtag   3900
aattctgttt caaactacct ggtggattta ttaattttgg atctgtatgt gtgtgccata   3960
catattcata gttacgaatt gaagatgatg gatggaaata tcgatctagg ataggtatac   4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aattttggaa ctgtatgtgt gtgtcataca tcttcatagt   4200
tacgagttta agatggatgg aaatatcgat ctaggatagg tatacatgtt gatgtgggtt   4260
ttactgatgc atatacatga tggcatatgc agcatctatt catatgctct aaccttgagt   4320
acctatctat tataataaac aagtatgttt tataattatt ttgatcttga tatacttgga   4380
tgatggcata tgcagcagct atatgtggat ttttttagcc ctgccttcat acgctattta   4440
tttgcttggt actgtttctt ttgtcgatgc tcaccctgtt gtttggtgtt acttctgcag   4500
gtcgactcta gaggatccaa caatggagaa caacatacag aatcagtgcg tcccctacaa   4560
ctgcctcaac aatcctgaag tagagattct caacgaagag aggtcgactg gcagattgcc   4620
gttagacatc tccctgtccc ttacacgttt cctgttgtct gagtttgttc caggtgtggg   4680
agttgcgttt ggcctcttcg acctcatctg gggcttcatc actccatctg attggagcct   4740
ctttcttctc cagattgaac agttgattga acaaaggatt gagaccttgg aaaggaatcg   4800
ggccatcact acccttcgtg gcttagcaga cagctatgag atctacattg aagcactaag   4860
agagtgggaa gccaatccta acaatgccca actgagagaa gatgtgcgta tacgctttgc   4920
taacacagat gatgctttga tcacagccat caacaacttc acccttacca gcttcgagat   4980
ccctcttctc tcggtctatg ttcaagctgc taacctgcac ttgtcactac tgcgcgacgc   5040
tgtgtcgttt gggcaaggtt ggggactgga catagctact gtcaacaatc actacaacag   5100
actcatcaat ctgattcatc gatacacgaa acattgtttg gatacctaca atcagggatt   5160
ggagaacctg agaggtacta acactcgcca atgggccagg ttcaatcagt tcaggagaga   5220
ccttacactt actgtgttag acatagttgc tctctttccg aactacgatg ttcgtaccta   5280
tccgattcaa acgtcatccc aacttacaag ggagatctac accagttcag tcattgaaga   5340
```

-continued

```
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt caacaaact ggtacgaatc acacccgcac     5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
taccccacac aacaccattg atccagagag aatcactcag attcccttgg tgaaggcaca    5940
cacacttcag tcaggaacta cagttgtaag agggccgggg ttcacgggag gagacattct    6000
tcgacgcact agtggaggac cattcgcgta caccattgtc aacatcaatg gcaacttcc     6060
ccaaaggtat cgtgccagga tacgctatgc ctctactacc aatctaagaa tctacgttac    6120
ggttgcaggt gaacggatct tgctggtca gttcaacaag acaatggata ccggtgatcc     6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt tcgttgcga ctaacatgag     6420
ttcttggaca aatttgattg gacctgatga atgatccaa cccgaggata tagcaaagct     6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttcataaag atcgaataga aaatactgca ctgcaaatga aaattaacac     6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccta cccgcgccca gtccggtgta agaacgggtc     7080
tgtccatcca cctctgttgg gaattccggt ccgggtcacc tttgtccacc aagatggaac    7140
tgcggccagc ttgcatgcct gcagtgcagc gtgacccgt cgtgccctc tctagagata     7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt   7440
gcatgtgttc tcctttttt ttgcaaatag cttcacctat ataatacttc atccatttta    7500
ttagtacatc catttagggt ttagggttaa tggttttat agactaattt ttttagtaca    7560
tctatttat tctatttag cctctaaatt aagaaaacta aaactctatt ttagtttttt      7620
tatttaataa tttagatata aaatagaata aaataaagtg actaaaaatt aaacaaatac    7680
ccttttaagaa attaaaaaaa ctaaggaaac attttttcttg tttcgagtag ataatgccag   7740
```

```
cctgttaaac gccgtcgacg agtctaacgg acaccaacca gcgaaccagc agcgtcgcgt   7800
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tcccttcctc gcccgccgta ataaatagac   8040 acccctcca caccctcttt ccccaacctc gtgttgttcg gagcgcacac acacacaacc   8100
agatctcccc caaatccacc cgtcggcacc tccgcttcaa ggtacgccgc tcgtcctccc   8160 ccccccccc tctctacctt ctctagatcg gcgttccggt ccatggttag ggcccggtag   8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400 tttttttgttt cgttgcatag ggttttggttt gcccttttcc tttatttcaa tatatgccgt   8460
gcacttgttt gtcgggtcat cttttcatgc ttttttttgt cttggttgtg atgatgtggt   8520
ctggttgggc ggtcgttcta gatcggagta gaattctgtt tcaaactacc tggtggattt   8580
attaattttg gatctgtatg tgtgtgccat acatattcat agttacgaat gaagatgat    8640 ggatggaaat atcgatctag gataggtata catgttgatg cgggttttac tgatgcatat   8700
acagagatgc tttttgttcg cttggttgtg atgatgtggt gtggttgggc ggtcgttcat   8760
tcgttctaga tcggagtaga atactgtttc aaactacctg gtgtatttat taattttgga   8820
actgtatgtg tgtgtcatac atcttcatag ttacgagttt aagatggatg gaaatatcga   8880
tctaggatag gtatacatgt tgatgtgggt tttactgatg catatacatg atggcatatg   8940
cagcatctat tcatatgctc taaccttgag tacctatcta ttataataaa caagtatgtt   9000
ttataattat tttgatcttg atatacttgg atgatggcat atgcagcagc tatatgtgga   9060 ttttttagc cctgccttca tacgctattt atttgcttgg tactgtttct tttgtcgatg    9120
ctcaccctgt tgtttggtgt tacttctgca ggtcgactct agaggatcca cacgacacca   9180
tgtccgcccg cgaggtgcac atcgacgtga acaacaagac cggccacacc ctccagctgg   9240
aggacaagac caagctcgac ggcggcaggt ggcgcacctc cccgaccaac gtggccaacg   9300
accagatcaa gaccttcgtg gccgaatcca acggcttcat gaccggcacc gagggcacca   9360
tctactactc aattaatggc gaggccgaga tcagcctcta cttcgacaac ccgttcgccg   9420
gctccaacaa atacgacggc cactccaaca agtcccagta cgagatcatc acccagggcg   9480
gctccggcaa ccagtcccac gtgacctaca ccatccagac cacctcctcc cgctacggcc   9540
acaagtcctg agtcatgagt catgagtcag ttaacctaga cttgtccatc ttctggattg   9600
gccaacttaa ttaatgtatg aaataaaagg atgcacacat agtgacatgc taatcactat   9660
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat atataattaa   9840
tatcaattgg gttagcaaaa caaatctagt ctaggtgtgt tttgcgaatg cggccgcgga   9900
ccgaattggg gatctgcatg aaagaaactg tcgcactgct gaaccgcacc ttgtcacttt   9960
catcgaacac gacctgtgcc caagatgacg gtgctgcggt ctaagtgagg ctgaattgcc  10020
ttggacagaa gcggactccc tacaattagt taggccaaac ggtgcatcca tgtgtagctc  10080
```

```
cgggctcggg ctgtatcgcc atctgcaata gcatccatgg agctcgttcc atgtagttgg   10140
agatgaacca atgatcgggc gtgtggacgt atgttcctgt gtactccgat agtgagtac    10200 gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgaccttct    10860 aaaaaatcgg cggctttgtc cgtatccgta tccctatcc aacatctagc tggccacacg    10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc    12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg ccaacttaa ttaatgtatg aaataaaagg atgcacacat agtgacatgc     12480
```

```
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccggaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg acccccacc cacgaggagc    13140 atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgatat    13380
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggttttg    13800 gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaccaaaat ccagggcgag ctcgaattcg agctcgagcc    14100
cgggtggatc tctagagtc gacctgcaga gcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccgg atataagaac ttcgatccga aatatcgttt    14340
caaaactaga aaacagcgcg gctttggcta agccgcgcac tatataggat tttgggcacc    14400
ttttgatgga acgtgaaagc gtactgcgca ctagttattt aggttgaacc ttggatatac    14460
ggttctcact gcgccaatgc aaggcttgaa acttggttag taatacgtac tccctccgtt    14520
tctttttatt tgtcgctgga tagtgcaatt ttgcactatc gagcgacaaa taaaagaaa    14580 cggagggagt atatgattgt cagatgtaga tatgtttatt tatatatcac atacagatat    14640
ataaaacaga tcactttttc agatatacag ttccaatgtc agccctgatc accctgtcat    14700
aaattgcacg tttctaattg atgttgcttc atggtcgtca tgagaacctt ctgaagaaat    14760
cgatgaaggt tgccaacctt tcaaagtttc agaaaccact ttgcatgtac actaagggct    14820
```

-continued

```
ggtttggcag cccaaaacca gccagcgttt tcctggtctt ttctcccggg agaaagccca    14880
tgcatagatt gtccctggat tatttatctg tgtcctttgg ctaaaaattc gtcccaattt    14940
cctgtaggaa actacctcgg ccttgggagg ccaggcgatt ctccaccgcc tcgtctcgtc    15000
catccttcga tgctcacgcg tgcctcctcg gatgctatcc tcaggcgatt ctccgtcgtc    15060
tcgtctcatc catcctcacg cgcgcctcct ccgacgctat ccccaggcga ttctccaccg    15120
tctcgtctca tccatcctca tgtacgcctc gtccgatgct atccccagac gattttccgt    15180
cgtctcatct ccttcatgct cgcgcgcgcc tcctccgacg ctatcccagg cgattttttc    15240
tgccgtctcg tctccttcat gcccgcgcgc gcctcctccg acgctatccc caggcgattt    15300
tccgccgtct cgtctccttc atgcccgcgc gtgcctcctc cgacgctatt cccacgagcg    15360
cctccgccgc cgctatcccc agacgattt ccgctgtctc gtctccttca tgcccgcgcg    15420
cccctcctcc gacgctatcc ccacgagcgc ctccgccgcc gctccaccgt cttcccgcc    15480 gccatccct taattcctat agatctggac cccgctctac tttcgttggc atactttgc    15540 ttggtgtgcg cgggctggag tggaaggttg cgcattcgat cacggggag aagtggatct    15600 tgggtcttgg caggctaggg cggttgccag gacgccgtgg tgtgcattca tgggtcctat    15660
aaatctttat cattaccgcc ttaggagcta gttgtagttc acacatcata tccttttctg    15720
ctcgacatcg tctggggatg ccctaggtgc cctaccgacc ctacggcatt gtcttgacct    15780
ctattagact ctatgtcatc tagagccttc ttgggtggcc ttttgacccc aaagcgaccc    15840
tatgatctta ccctaacgag gtctccttg gtggggcaag atccactttg tccacttaac    15900
tgaagatctg atcctcatct tgaaatcttt aatcccaagg tgactctacg tcgtatgtgg    15960
atgctccggg taacctgcca acccggatca ccctaagatc tctttcctaa ggggcgagat    16020
ctaggttcct acgagaaaga agacgaccct gcaccattgc ggtccgtccg gtccagagtg    16080
cgaacgtccg gatgcgacac agggaaggag tcgctcctgc agcgaggtcg cagactgtcc    16140
acacagcctc agaaggcacc gccagacaat acatgtaata cccactctgt aagaaaaacc    16200
taaaaggaga agtatattc ctttatctat atgtgtgtta tatttctact caccatcaca    16260
tgtgaacatc tcacttacac aaataaataa ttaacaaaag acactcaaat aaattatgca    16320
tcatgctcga ccttatttg tgtgcattct gttacaatat aaaaataata taaaaacat    16380 atattaatat caaatttgg agatttaacc ctaatatgca aatcggagtt tagaggaaag    16440
aaagaaaaat gctatacaaa ataaaggaat aaatatataa ataaggtaa aactattaat    16500 actggtatat taatttgaac agttgaccta attatgaata tcacaactgg tttgaattca    16560
aatatgaaat ccaagaattt ggaaatagga aaatggaga taagaataaa ggaaagaat    16620 tcttaactcg gatgggcctg ggaaacgaat ttcggcccac ttcctgtgtc cttagctgtg    16680
cggctcagtc cagtg                                                    16695
```

```
<210> SEQ ID NO 3
<211> LENGTH: 16699
<212> TYPE: DNA
<213> ORGANISM: Artificial
<220> FEATURE:
<223> OTHER INFORMATION: synthetic

<400> SEQUENCE: 3
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
```

```
gatgttgatg attggtctag agctagaggc ctatagccct atactactgt gtattgtccg      240 ccgtttagt  ttttggtcc  catcccatca atgcaaccgc cttgttttgc tccaattgtc      300
ccgttcctgc gcctcgcttt tgctctgtcg catcgcatac aaaaaaaaaa acgccgcgcc      360
ggctttgaat cgcgccccc  aactgctcca accaggcaac ggacacgcc  accgtccgtg      420 tcgcgagcaa aaaacaaaa  agaggaacgc gtccaggacg aagcagtcca ctgccgctgt      480
ggccggcaaa gatctggtt  gagcacatgg agattggaga aggttggttg gttcttctgg      540
aaacgccaat gaatggggc  actgacatgt actcttaaca tgtagtgcaa tccagagatc      600
ggatatccag acactggcag cacgatcgcc tcgcgccgta gatcacgcac gcaaattact      660
gaagaccatt cacaaaaaaa aaaaaacaca caggggctag cgtgccccac accaaaccca      720
agtgctgcgt tgcacgcagg ggagcgaaaa aaaacaataa tgctcactgt cacgtcgcgt      780
atccaacccc gcggacgtct cggctctcag cagcagcaca cggggcacct cacgatgccg      840
ttctcgttgc actccgtgca ccgccggaac ccgccgccgc attcgtcgcc ctcctcctcc      900
tcctccgcct cgtcttcgtc acccacgtac accttgcagc tgcccgagca gacatcgcag      960
agcacgaacc gcatgtcccc gcaggcctcg cacgcgccgg cgtcgccgcc gtgtgggccg     1020
gccgtcgacg cagcgctctc gcacccggcc agcctcggcg cgagctcccc ggcctcgtgc     1080
agccgcttca gctcctcggc gttgcccacg agctccccgt ccacgaagag gctggggagg     1140
gcggcgggcg tgccgccggc ttggccgagc ccgaggccga aaggccgcg  gagctcgtcc     1200 cggaacccgc ggtgcatgga cacgtcgcgc tcgtcgaggc gcacgccgta gcccttgagg     1260
atggcgcgcg ccaggcagca gtcctcgtgc gtggcgcgca cgccgcgcag cgacgtgaag     1320
tagagcaccg ccctccgcgg cggcagcgcc ttcccctccc cgccgctcgt cggggcggcg     1380
tcgggccgag gcatcggcat cggcagcggc gtcaccttgg cggacgccgc gaggtcctgc     1440
gcaggcgccg tggcgaccgg gaacgagaag gagtggcgcc cgaacggcgc gcccagcagc     1500
ggggagcggt cctcgaggcc ggccatgagc gcccacgcgt cgatgtcctc gggctcgttg     1560
ggcggcgtca tggtgggcgt gcgcggcgcc agcctcgtgg gcgcgggctc cggcgcccgc     1620
ggcagggcct tgtccagctc cagggacccg agcgtggacg acgtgagccg caccacgtgg     1680
acgccgacgt cgctggggca ccgagccggg aacgactggc tgcgcggcag cggtgacggg     1740
cagtaccgga ggtcgtgacg ggcctgcctt gaggtggtgc accccatggc accaatgtac     1800
acacacggcc aaagcgccaa gtgggctgca gactgcctgc caatgtgatc aagcagccag     1860
gagcagagac ggatctctgg ggatcggggt ttctggggtt taggatcttt atactactct     1920
gtcattgggg atataaaact aggagtgtgg ttaattagga ctcgatagat aagtttacca     1980
caagcgcgtg aaatggtcta cccgatgatg tgattggcct aaaagaaca  agaagagtat     2040 ttggagctac tgaacattct cttttcctga agataactaa ttttggaac  attcagactt     2100 gggagtctgg acttttggag ggaagttcaa attgtggtct gcctctgcca tgtgttgttt     2160
tttagtcgga gagtggccct cattttttt  gtcctgttta gctttatagt cgtagcagct     2220
agtagcgaaa tttaaccttg gattatggcc gtgttagtca aacaatcatt gatttatttc     2280 ctcccttcg  cgctgctttt cctgtacgca tctccgctgc ccttgattcg aggaccctgt     2340
tcacaacaca gggctctggc tttggagcct ctcgtttgta gcacttgcac gtagttaccc     2400
ggaccgaagc ttcaacacag atctgatagt ttaaacgctc ttcaactgga agagcggtta     2460
cccggaccga agcttcggcc ggggcccatc gatatccgcg gcatgcctg  cagtgcagcg     2520
```

```
tgacccggtc gtgcccctct ctagagataa tgagcattgc atgtctaagt tataaaaaat    2580
taccacatat ttttttttgtc acacttgttt gaagtgcagt ttatctatct ttatacatat   2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct ccttttttt tgcaaatagc     2820 ttcacctata taatacttca tccattttat tagtacatcc atttagggtt tagggttaat    2880
ggtttttata gactaatttt tttagtacat ctatttatt ctatttagc ctctaaatta     2940 agaaaactaa aactctattt tagtttttt atttaataat ttagatataa aatagaataa     3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga   3120
caccaaccag cgaaccagca gcgtcgcgtc gggccaagcg aagcagacgg cacggcatct   3180
ctgtcgctgc ctctggaccc ctctcgagag ttccgctcca ccgttggact tgctccgctg   3240
tcggcatcca gaaattgcgt ggcggagcgg cagacgtgag ccggcacggc aggcggcctc   3300
ctcctcctct cacggcaccg gcagctacgg gggattcctt tcccaccgct ccttcgcttt   3360
cccttcctcg cccgccgtaa taaatagaca ccccctccac accctctttc cccaacctcg   3420
tgttgttcgg agcgcacaca cacacaacca gatctccccc aaatccaccc gtcggcacct   3480
ccgcttcaag gtacgccgct cgtcctcccc ccccccccct ctctaccttc tctagatcgg   3540
cgttccggtc catggttagg gcccggtagt tctacttctg ttcatgtttg tgttagatcc   3600
gtgtttgtgt tagatccgtg ctgctagcgt tcgtacacgg atgcgacctg tacgtcagac   3660
acgttctgat tgctaacttg ccagtgtttc tcttttggga atcctgggat ggctctagcc   3720
gttccgcaga cgggatcgat ttcatgattt ttttgtttc gttgcatagg gtttggtttg    3780 ccctttttcct ttatttcaat atatgccgtg cacttgtttg tcgggtcatc ttttcatgct   3840 ttttttttgtc ttggttgtga tgatgtggtc tggttgggcg gtcgttctag atcggagtag  3900
aattctgttt caaactacct ggtggattta ttaattttgg atctgtatgt gtgtgccata   3960
catattcata gttacgaatt gaagatgatg gatggaaata tcgatctagg ataggtatac   4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aattttggaa ctgtatgtgt gtgtcataca tcttcatagt   4200
tacgagttta agatggatgg aaatatcgat ctaggatagg tatacatgtt gatgtgggtt   4260
ttactgatgc atatacatga tggcatatgc agcatctatt catatgctct aaccttgagt   4320
acctatctat tataataaac aagtatgttt tataattatt ttgatcttga tatacttgga   4380
tgatggcata tgcagcagct atatgtggat tttttagcc ctgccttcat acgctattta    4440
tttgcttggt actgtttctt ttgtcgatgc tcaccctgtt gtttggtgtt acttctgcag   4500
gtcgactcta gaggatccaa caatgaagaa caacatacag aatcagtgcg tcccctacaa   4560
ctgcctcaac aatcctgaag tagagattct caacgaagag aggtcgactg gcagattgcc   4620
gttagacatc tccctgtccc ttacacgttt cctgttgtct gagtttgttc caggtgtggg   4680
agttgcgttt ggcctcttcg acctcatctg gggcttcatc actccatctg attggagcct   4740
ctttcttctc cagattgaac agttgattga acaaaggatt gagaccttgg aaaggaatcg   4800
ggccatcact acccttcgtg gcttagcaga cagctatgag atctacattg aagcactaag   4860
agagtgggaa gccaatccta acaatgccca actgagagaa gatgtgcgta tacgctttgc   4920
```

```
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca acaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg ggcaacttcc    6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccatc ccgcgcccaa gtccggtgta agaacgggtc    7080
tgtccatcca cctctgttgg gaattccggt ccgggtcacc tttgtccacc aagatggaac    7140
tgcggccagc ttgcatgcct gcagtgcagc gtgaccccgt cgtgcccctc tctagagata    7200
atgagcattg catgtctaag ttataaaaaa ttaccacata tttttttttgt cacacttgtt    7260
```

```
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt   7440 gcatgtgttc tcctttttt ttgcaaatag cttcacctat ataatacttc atccatttta    7500
ttagtacatc catttagggt ttagggttaa tggtttttat agactaattt ttttagtaca    7560 tctatttat tctattttag cctctaaatt aagaaaacta aaactctatt ttagtttttt     7620
tatttaataa tttagatata aaatagaata aaataaagtg actaaaaatt aaacaaatac    7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160 ccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400 tttttgttt cgttgcatag ggtttggttt gccctttcc tttatttcaa tatatgccgt      8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttccatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060 ttttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca gtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
```

```
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620 aaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttcccctat   11100 aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
```

```
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccggaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg gacccccacc cacgaggagc    13140
atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgatat    13380
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc tctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccgg ccagatataa gaacttcgat ccgaaatatc    14340
gtttcaaaac tagaaaacag cgcggctttg gctaagccgc gcactatata ggattttggg    14400
```

```
cacctttttga tggaacgtga aagcgtactg cgcactagtt atttaggttg aaccttggat   14460
atacggttct cactgcgcca atgcaaggct tgaaacttgg ttagtaatac gtactccctc   14520
cgtttctttt tatttgtcgc tggatagtgc aattttgcac tatcgagcga caaataaaaa   14580
gaaacggagg gagtatatga ttgtcagatg tagatatgtt tatttatata tcacatacag   14640
atatataaaa cagatcactt tttcagatat acagttccaa tgtcagccct gatcaccctg   14700
tcataaattg cacgtttcta attgatgttg cttcatggtc gtcatgagaa ccttctgaag   14760
aaatcgatga aggttgccaa cctttcaaag tttcagaaac cactttgcat gtacactaag   14820
ggctggtttg gcagcccaaa accagccagc gttttcctgg tcttttctcc cgggagaaag   14880
cccatgcata gattgtccct ggattattta tctgtgtcct ttggctaaaa attcgtccca   14940
atttcctgta ggaaactacc tcggccttgg gaggccaggc gattctccac cgcctcgtct   15000
cgtccatcct tcgatgctca cgcgtgcctc ctcggatgct atcctcaggc gattctccgt   15060
cgtctcgtct catccatcct cacgcgcgcc tcctccgacg ctatccccag gcgattctcc   15120
accgtctcgt ctcatccatc ctcatgtacg cctcgtccga tgctatcccc agacgatttt   15180
ccgtcgtctc atctccttca tgctcgcgcg cgcctcctcc gacgctatcc ccaggcgatt   15240
tttctgccgt ctcgtctcct tcatgcccgc gcgcgcctcc tccgacgcta tccccaggcg   15300
attttccgcc gtctcgtctc cttcatgccc gcgcgtgcct cctccgacgc tattcccacg   15360
agcgcctccg ccgccgctat ccccagacga ttttccgctg tctcgtctcc ttcatgcccg   15420
cgcgcccctc ctccgacgct atccccacga gcgcctccgc cgccgctcca ccgtcttccc   15480
cgccgccatc cccttaattc ctatagatct ggaccccgct ctactttcgt tggcatactt   15540
ttgcttggtg tgcgcgggct ggagtggaag gttgcgcatt cgatcacggg ggagaagtgg   15600
atcttgggtc ttggcaggct agggcggttg ccaggacgcc gtggtgtgca ttcatgggtc   15660
ctataaatct ttatcattac cgccttagga gctagttgta gttcacacat catatccttt   15720
tctgctcgac atcgtctggg gatgccctag gtgccctacc gaccctacgg cattgtcttg   15780
acctctatta gactctatgt catctagagc cttcttgggt ggccttttga ccccaaagcg   15840
accctatgat cttaccctaa cgaggtctcc cttggtgggg caagatccac tttgtccact   15900
taactgaaga tctgatcctc atcttgaaat cttaatccc aaggtgactc tacgtcgtat   15960
gtggatgctc cgggtaacct gccaacccgg atcaccctaa gatctctttc ctaaggggcg   16020
agatctaggt tcctacgaga aagaagacga ccctgcacca ttgcggtccg tccggtccag   16080
agtgcgaacg tccggatgcg acacagggaa ggagtcgctc ctgcagcgag gtcgcagact   16140
gtccacacag cctcagaagg caccgccaga caatacatgt aatacccact ctgtaagaaa   16200
aacctaaaag gagaaagtat attccttat ctatatgtgt gttatatttc tactcaccat   16260
cacatgtgaa catctcactt acacaaataa ataattaaca aaagacactc aaataaatta   16320
tgcatcatgc tcgaccttat tttgtgtgca ttctgttaca atataaaaat aatataaaaa   16380
acatatatta atatcaaaat ttggagattt aaccctaata tgcaaatcgg agtttagagg   16440
aaagaaagaa aaatgctata caaaataaag gaataaatat ataaataaag gtaaaactat   16500
taatactggt atattaattt gaacagttga cctaattatg aatatcacaa ctggtttgaa   16560
ttcaaatatg aaatccaaga atttggaaat aggaaaaatg gagataagaa taaggaaaa   16620 gaattcttaa ctcggatggg cctgggaaac gaatttcggc ccacttcctg tgtccttagc   16680
tgtgcggctc agtccagtg                                                16699
```

```
<210> SEQ ID NO 4
<211> LENGTH: 23
<212> TYPE: DNA
<213> ORGANISM: Artificial
<220> FEATURE:
<223> OTHER INFORMATION: synthetic

<400> SEQUENCE: 4
gaacaagtgg ctatcgccag ata                                              23

<210> SEQ ID NO 5
<211> LENGTH: 23
<212> TYPE: DNA
<213> ORGANISM: Artificial
<220> FEATURE:
<223> OTHER INFORMATION: synthetic

<400> SEQUENCE: 5
atgtactgaa ttgtctagta gcg                                              23

<210> SEQ ID NO 6
<211> LENGTH: 23
<212> TYPE: DNA
<213> ORGANISM: Artificial
<220> FEATURE:
<223> OTHER INFORMATION: synthetic

<400> SEQUENCE: 6
ggatcgaagt tcttatatct ggc                                              23

<210> SEQ ID NO 7
<211> LENGTH: 27
<212> TYPE: DNA
<213> ORGANISM: Artificial
<220> FEATURE:
<223> OTHER INFORMATION: synthetic

<400> SEQUENCE: 7
tttgtagcac ttgcacgtag ttacccg                                          27

<210> SEQ ID NO 8
<211> LENGTH: 35
<212> TYPE: DNA
<213> ORGANISM: Artificial
<220> FEATURE:
<223> OTHER INFORMATION: synthetic

<400> SEQUENCE: 8
cgcttttgta gcacttgcac gtagttaccc ggata                                 35

<210> SEQ ID NO 9
<211> LENGTH: 64
<212> TYPE: DNA
<213> ORGANISM: Artificial
<220> FEATURE:
<223> OTHER INFORMATION: synthetic

<400> SEQUENCE: 9
aacgtgcaag cgcttttgta gcacttgcac gtagttaccc ggatataaga acttcgatcc      60
gaaa                                                                   64

<210> SEQ ID NO 10
<211> LENGTH: 68
<212> TYPE: DNA
<213> ORGANISM: Artificial
```

```
<220> FEATURE:
<223> OTHER INFORMATION: synthetic

<400> SEQUENCE: 10
aacgtgcaag cgcttttgta gcacttgcac gtagttaccc ggccagatat aagaacttcg      60
atccgaaa                                                               68

<210> SEQ ID NO 11
<211> LENGTH: 31
<212> TYPE: DNA
<213> ORGANISM: Artificial
<220> FEATURE:
<223> OTHER INFORMATION: synthetic

<400> SEQUENCE: 11
cgcttttgta gcacttgcac gtagttaccc g                                     31

<210> SEQ ID NO 12
<211> LENGTH: 31
<212> TYPE: DNA
<213> ORGANISM: Artificial
<220> FEATURE:
<223> OTHER INFORMATION: synthetic

<400> SEQUENCE: 12
tatccgggta actacgtgca agtgctacaa a                                     31

<210> SEQ ID NO 13
<211> LENGTH: 31
<212> TYPE: DNA
<213> ORGANISM: Artificial
<220> FEATURE:
<223> OTHER INFORMATION: synthetic

<400> SEQUENCE: 13
tggccgggta actacgtgca agtgctacaa a                                     31

<210> SEQ ID NO 14
<211> LENGTH: 1227
<212> TYPE: DNA
<213> ORGANISM: Artificial
<220> FEATURE:
<223> OTHER INFORMATION: synthetic

<400> SEQUENCE: 14
ttataggcct tccaaacgat ccatctgtta ggttgcatga ggctttggga tacacagccc       60
ggggtacatt gcgcgcagct ggatacaagc atggtggatg catgatgtt ggttttggc       120 aaagggattt tgagttgcca gctcctccaa ggccagttag gccagttacc cagatctgag     180
tcgacctgca gcatgcccg ctgaaatcac cagtctctct ctacaaatct atctctctct      240
ataataatgt gtgagtagtt cccagataag ggaattaggg ttcttatagg gtttcgctca     300
tgtgttgagc atataagaaa ccctagtat gtatttgtat ttgtaaaata cttctatcaa      360
taaaatttct aattcctaaa accaaaatcc agggcgagct cgaattcgag ctcgagcccg     420
ggtggatcct ctagagtcga cctgcagaag cttcggtccg gcgcgcctct agttgaagac     480
acgttcatgt cttcatcgta agaagacact cagtagtctt cggccagaat ggcctaactc     540
aaggccatcg tggcctcttg ctcttcagga tgaagagcta tgtttaaacg tgcaagcgct     600
tttgtagcac ttgcacgtag ttacccgact agacaattca gtacattaaa acgtccgca      660 atgtgttatt aagttgtcta agcgtcaatt tggaacaagt ggctatcgcc agatataaga     720
```

```
acttcgatcc gaaatatcgt ttcaaaacta gaaaacagcg cggctttggc taagccgcgc    780
actatatagg attttgggca ccttttgatg gaacgtgaaa gcgtactgcg cactagttat    840
ttaggttgaa ccttggatat acggttctca ctgcgccaat gcaaggcttg aaacttggtt    900
agtaatacgt actccctccg tttcttttta tttgtcgctg gatagtgcaa ttttgcacta    960
tcgagcgaca aataaaaaga aacggaggga gtatatgatt gtcagatgta gatatgttta   1020
tttatatatc acatacagat atataaaaca gatcactttt tcagatatac agttccaatg   1080
tcagccctga tcaccctgtc ataaattgca cgtttctaat tgatgttgct tcatggtcgt   1140
catgagaacc ttctgaagaa atcgatgaag gttgccaacc tttcaaagtt tcagaaacca   1200
ctttgcatgt acactaaggg ctggttt                                       1227
```

```
<210> SEQ ID NO 15
<211> LENGTH: 27
<212> TYPE: DNA
<213> ORGANISM: Artificial
<220> FEATURE:
<223> OTHER INFORMATION: synthetic

<400> SEQUENCE: 15
cgctactaga caattcagta cattaaa                                         27

<210> SEQ ID NO 16
<211> LENGTH: 24
<212> TYPE: DNA
<213> ORGANISM: Artificial
<220> FEATURE:
<223> OTHER INFORMATION: synthetic

<400> SEQUENCE: 16
atgtactgaa ttgtctagta gcgc                                            24

<210> SEQ ID NO 17
<211> LENGTH: 25
<212> TYPE: DNA
<213> ORGANISM: Artificial
<220> FEATURE:
<223> OTHER INFORMATION: synthetic

<400> SEQUENCE: 17
tacgctgggc cctggaaggc tagga                                           25

<210> SEQ ID NO 18
<211> LENGTH: 25
<212> TYPE: DNA
<213> ORGANISM: Artificial
<220> FEATURE:
<223> OTHER INFORMATION: synthetic

<400> SEQUENCE: 18
gatggacgag acgaggcggt ggaga                                           25

<210> SEQ ID NO 19
<211> LENGTH: 46
<212> TYPE: DNA
<213> ORGANISM: Artificial
<220> FEATURE:
<223> OTHER INFORMATION: synthetic

<400> SEQUENCE: 19
tgcaagcgct tttgtagcac ttgcacgtag ttacccgact agacaa                    46
```

<210> SEQ ID NO 20
<211> LENGTH: 16779
<212> TYPE: DNA
<213> ORGANISM: Artificial
<220> FEATURE:
<223> OTHER INFORMATION: synthetic

<400> SEQUENCE: 20

| | | | | | | |
|---|---|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgttttagt | tttttggtcc | catcccatca | atgcaaccgc | cttgttttgc | tccaattgtc | 300 |
| ccgttcctgc | gcctcgcttt | tgctctgtcg | catcgcatac | aaaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcacccggcc | agcctcggcg | cgagctcccc | ggcctcgtgc | 1080 |
| agccgcttca | gctcctcggc | gttgcccacg | agctccccgt | ccacgaagag | gctggggagg | 1140 |
| gcggcgggcg | tgccgccggc | ttggccgagc | ccgaggccga | aaggccgcg | agctcgtcc | 1200 |
| cggaacccgc | ggtgcatgga | cacgtcgcgc | tcgtcgaggc | gcacgccgta | gcccttgagg | 1260 |
| atggcgcgcg | ccaggcagca | gtcctcgtgc | gtggcgcgca | cgccgcgcag | cgacgtgaag | 1320 |
| tagagcaccg | ccctccgcgg | cggcagcgcc | ttcccctccc | cgccgctcgt | cggggcggcg | 1380 |
| tcgggccgag | gcatcggcat | cggcagcggc | gtcaccttgg | cggacgccgc | gaggtcctgc | 1440 |
| gcaggcgccg | tggcgaccgg | gaacgagaag | gagtggcgcc | cgaacggcgc | gcccagcagc | 1500 |
| ggggagcggt | cctcgaggcc | ggccatgagc | gcccacgcgt | cgatgtcctc | gggctcgttg | 1560 |
| ggcggcgtca | tggtgggcgt | gcgcggcgcc | agcctcgtgg | gcgcgggctc | cggcgcccgc | 1620 |
| ggcagggcct | tgtccagctc | cagggacccg | agcgtggacg | acgtgagccg | caccacgtgg | 1680 |
| acgccgacgt | cgctggggca | ccgagccggg | aacgactggc | tgcgcggcag | cggtgacggg | 1740 |
| cagtaccgga | ggtcgtgacg | ggcctgcctt | gaggtggtgc | accccatggc | accaatgtac | 1800 |
| acacacggcc | aaagcgccaa | gtgggctgca | gactgcctgc | caatgtgatc | aagcagccag | 1860 |
| gagcagagac | ggatctctgg | ggatcggggt | ttctggggtt | taggatcttt | atactactct | 1920 |
| gtcattgggg | atataaaact | aggagtgtgg | ttaattagga | ctcgatagat | aagtttacca | 1980 |
| caagcgcgtg | aaatggtcta | cccgatgatg | tgattggcct | aaaaagaaca | agaagagtat | 2040 |
| ttggagctac | tgaacattct | cttttcctga | agataactaa | ttttggaac | attcagactt | 2100 |

```
gggagtctgg acttttggag ggaagttcaa attgtggtct gcctctgcca tgtgttgttt    2160
tttagtcgga gagtggccct catttttttt gtcctgttta gctttatagt cgtagcagct    2220
agtagcgaaa tttaaccttg gattatggcc gtgttagtca acaatcatt gatttatttc     2280
ctcccttttcg cgctgctttt cctgtacgca tctccgctgc ccttgattcg aggaccctgt   2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg ggcatgcctg cagtgcagcg    2520
tgacccggtc gtgcccctct ctagagataa tgagcattgc atgtctaagt tataaaaaat    2580
taccacatat tttttttgtc acacttgttt gaagtgcagt ttatctatct ttatacatat    2640
atttaaactt tactctacga ataatataat ctatagtact acaataatat cagtgtttta    2700
gagaatcata taaatgaaca gttagacatg gtctaaagga caattgagta ttttgacaac    2760
aggactctac agtttatct ttttagtgtg catgtgttct ccttttttt tgcaaatagc       2820
ttcacctata taatacttca tccatttat tagtacatcc atttagggtt tagggttaat      2880
ggtttttata gactaatttt tttagtacat ctattttatt ctattttagc ctctaaatta    2940
agaaaactaa aactctattt tagtttttttt atttaataat ttagatataa aatagaataa   3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga   3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt     3360
cccttcctcg cccgccgtaa taaatagaca cccccctccac accctctttc cccaacctcg   3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tcttgggga atcctgggat ggctctagcc    3720
gttccgcaga cgggatcgat ttcatgattt ttttttgtttc gttgcatagg gtttggtttg   3780
cccttttcct ttatttcaat atatgccgtg cacttgtttg tcgggtcatc ttttcatgct    3840
ttttttttgtc ttggttgtga tgatgtggtc tggttgggcg gtcgttctag atcggagtag   3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aattttggaa ctgtatgtgt gtgtcataca tcttcatagt   4200
tacgagttta agatggatgg aaatatcgat ctaggatagg tatacatgtt gatgtgggtt   4260
ttactgatgc atatacatga tggcatatgc agcatctatt catatgctct aaccttgagt   4320
acctatctat tataataaac aagtatgttt tataattatt ttgatcttga tatacttgga   4380
tgatggcata tgcagcagct atatgtggat ttttttagcc ctgccttcat acgctattta   4440
tttgcttggt actgtttctt ttgtcgatgc tcaccctgtt gtttggtgtt acttctgcag   4500
```

```
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca aacaccattg atccagagag aatcactcag attcccttgg tgaaggcaca    5940
cacacttcag tcaggaacta cagttgtaag agggccgggg ttcacgggag gagacattct    6000
tcgacgcact agtggaggac cattcgcgta caccattgtc aacatcaatg ggcaacttcc    6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtatttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
```

```
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgccctc tctagagata    7200
atgagcattg catgtctaag ttataaaaaa ttaccacata tttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttagtgt    7440
gcatgtgttc tcctttttt ttgcaaatag cttcacctat ataatacttc atccatttta    7500
ttagtacatc catttagggt ttaggttaa tggttttat agactaattt ttttagtaca    7560
tctatttat tctattttag cctctaaatt aagaaaacta aaactctatt ttagttttt    7620
tatttaataa tttagatata aaatagaata aaataaagtg actaaaaatt aaacaaatac    7680
cctttaagaa attaaaaaaa ctaaggaaac attttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tccttcctc gcccgccgta ataaatagac    8040
accccctcca caccctcttt ccccaactc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
tttttgttt cgttgcatag ggtttggttt gcccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
```

```
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc aagatgacg gtgctgcggt ctaagtgagg ctgaattgcc    10020
ttggacagaa gcggactccc tacaattagt taggccaaac ggtgcatcca tgtgtagctc    10080
cgggctcggg ctgtatcgcc atctgcaata gcatccatgg agctcgttcc atgtagttgg    10140
agatgaacca atgatcgggc gtgtggacgt atgttcctgt gtactccgat agtgagagtac   10200 gtgttagctc tttcatggtg caagtgaaat ttgtgttggt ttaattaccc ctacgttagt    10260
tgcgggacag gagacacatc atgaatttaa aggcgatgat gtcctctcct gtaatgttat    10320
tcttttgatg tgatgaatca aaatgtcata taaaacattt gttgctcttt agttaggcct    10380
gatcgtagaa cgaaatgctc gtgtagcggg gctacgagcc tatgacgcaa taacactggt    10440
ttgccggccc ggagtcgctt gacaaaaaaa agcatgttaa gtttatttac aattcaaaac    10500
ctaacatatt atattccctc aaagcaggtt cacgatcaca cctgtaccta aaaaaaacat    10560
gaagaatata ttactccatt attatgagat gaaccacttg gcaagagtgg taagctatat    10620
aaaaaaatga acattattac gagatgttat atgccattat attgattcga agatatatgt    10680
ttctttctcc cacgggcacc taacggatac atgataaggc caaggcagat cacgggaaat    10740
tattcgaata catgttacgc cctattgccg gaaaaaaaat gcagggcagg tgttggccgt    10800
agcgatttaa gcacttaagc tggaggttgc cacacttgga tgcaagcgtc tgacccttct    10860
aaaaaatcgg cggctttgtc cgtatccgta tccctatcc aacatctagc tggccacacg    10920
acggggctgg gcagatcgtg gatgccgggt cgacgtcgat cgtcagccat catagaccaa    10980
tcgaccatct gttatggatg cttgctagct agactagtca gacataaaat ttggatactt    11040
tctcccaact gggagacggg gactgatgtg cagctgcacg tgagctaaat ttttcccctat   11100 aaatatgcat gaaatactgc attatcttgc cacagccact gccacagcca gataacaagt    11160
gcagctggta gcacgcaacg catagctctg gacttgtagc taggtagcca accggatcca    11220
cacgacacca tgctcgacac caacaaggtg tacgagatca gcaaccacgc caacggcctc    11280
tacgccgcca cctacctctc cctcgacgac tccggcgtgt ccctcatgaa caagaacgac    11340
gacgacatcg acgactacaa cctcaagtgg ttcctcttcc cgatcgacga cgaccagtac    11400
atcatcacct cctacgccgc caacaactgc aaggtgtgga acgtgaacaa cgacaagatt    11460
aatgtgtcaa cctactcctc caccaactcc atccagaagt ggcagatcaa ggccaacggc    11520
tcctcctacg tgatccagtc cgacaacggc aaggtgctca ccgccggcac cggccaggcc    11580
```

```
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
taatcactat aatgtgggca tcaaagttgt gtgttatgtg taattactag ttatctgaat   12540
aaaagagaaa gagatcatcc atatttctta tcctaaatga atgtcacgtg tcttataat   12600 tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccggccgaa gctggccgcg gaccgaattc ccatggagtc aaagattcaa   12780
atagaggacc taacagaact cgccgtaaag actggcgaac agttcataca gagtctctta   12840
cgactcaatg acaagaagaa aatcttcgtc aacatggtgg agcacgacac gcttgtctac   12900
tccaaaaata tcaaagatac agtctcagaa gaccaagggg caattgagac ttttcaacaa   12960
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg acccccacc cacgaggagc   13140 atcgtggaaa aagaagacgt tccaaccacg tcttcaaagc aagtggattg atgtgatatc   13200
tccactgacg taagggatga cgcacaatcc cactatcctt cgcaagaccc ttcctctata   13260
taaggaagtt catttcattt ggagaggaca gggtacccgg ggatccacca tgtctccgga   13320
gaggagacca gttgagatta ggccagctac agcagctgat atggccgcgg tttgtgatat   13380
cgttaaccat tacattgaga cgtctacagt gaactttagg acagagccac aaacaccaca   13440
agagtggatt gatgatctag agaggttgca agatagatac ccttggttgg ttgctgaggt   13500
tgagggtgtt gtggctggta ttgcttacgc tgggccctgg aaggctagga acgcttacga   13560
ttggacagtt gagagtactg tttacgtgtc acataggcat caaaggttgg gcctaggatc   13620
cacattgtac acacatttgc ttaagtctat ggaggcgcaa ggttttaagt ctgtggttgc   13680
tgttataggc cttccaaacg atccatctgt taggttgcat gaggctttgg gatacacagc   13740
ccggggtaca ttgcgcgcag ctggatacaa gcatggtgga tggcatgatg ttggttttg   13800 gcaaagggat tttgagttgc cagctcctcc aaggccagtt aggccagtta cccagatctg   13860
agtcgacctg caggcatgcc cgctgaaatc accagtctct ctctacaaat ctatctctct   13920
ctataataat gtgtgagtag ttcccagata agggaattag ggttcttata gggtttcgct   13980
```

```
catgtgttga gcatataaga aaccettagt atgtatttgt atttgtaaaa tacttctatc    14040
aataaaattt ctaattccta aaaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccga ctagacaatt cagtacatta aaaacgtccg    14340
caatgtgtta ttaagttgtc taagcgtcaa tttggaacaa gtggctatcg ccagatataa    14400
gaacttcgat ccgaaatatc gtttcaaaac tagaaaacag cgcggctttg gctaagccgc    14460
gcactatata ggattttggg caccttttga tggaacgtga aagcgtactg cgcactagtt    14520
atttaggttg aaccttggat atacggttct cactgcgcca atgcaaggct tgaaacttgg    14580
ttagtaatac gtactccctc cgtttctttt tatttgtcgc tggatagtgc aattttgcac    14640
tatcgagcga caaataaaaa gaaacggagg gagtatatga ttgtcagatg tagatatgtt    14700
tatttatata tcacatacag atatataaaa cagatcactt tttcagatat acagttccaa    14760
tgtcagccct gatcaccctg tcataaattg cacgtttcta attgatgttg cttcatggtc    14820
gtcatgagaa ccttctgaag aaatcgatga aggttgccaa cctttcaaag tttcagaaac    14880
cactttgcat gtacactaag ggctgggttg gcagcccaaa accagccagc gttttcctgg    14940
tcttttctcc cgggagaaag cccatgcata gattgtccct ggattattta tctgtgtcct    15000
ttggctaaaa attcgtccca atttcctgta ggaaactacc tcggccttgg gaggccaggc    15060
gattctccac cgcctcgtct cgtccatcct tcgatgctca cgcgtgcctc ctcggatgct    15120
atcctcaggc gattctccgt cgtctcgtct catccatcct cacgcgcgcc tcctccgacg    15180
ctatccccag gcgattctcc accgtctcgt ctcatccatc ctcatgtacg cctcgtccga    15240
tgctatcccc agacgatttt ccgtcgtctc atctccttca tgctcgcgcg cgcctcctcc    15300
gacgctatcc ccaggcgatt tttctgccgt ctcgtctcct tcatgcccgc gcgcgcctcc    15360
tccgacgcta tccccaggcg attttccgcc gtctcgtctc cttcatgccc gcgcgtgcct    15420
cctccgacgc tattcccacg agcgcctccg ccgccgctat ccccagacga ttttccgctg    15480
tctcgtctcc ttcatgcccg cgcgccctc ctccgacgct atcccacga gcgcctccgc    15540
cgccgctcca ccgtcttccc cgccgccatc ccttaattc ctatagatct ggaccccgct    15600
ctactttcgt tggcatactt ttgcttggtg tgcgcgggct ggagtggaag gttgcgcatt    15660
cgatcacggg ggagaagtgg atcttgggtc ttggcaggct agggcggttg ccaggacgcc    15720
gtggtgtgca ttcatgggtc ctataaatct ttatcattac cgccttagga gctagttgta    15780
gttcacacat catatccttt tctgctcgac atcgtctggg gatgccctag gtgccctacc    15840
gaccctacgg cattgtcttg acctctatta gactctatgt catctagagc cttcttgggt    15900
ggccttttga ccccaaagcg accctatgat cttaccctaa cgaggtctcc cttggtgggg    15960
caagatccac tttgtccact taactgaaga tctgatcctc atcttgaaat ctttaatccc    16020
aaggtgactc tacgtcgtat gtggatgctc cgggtaacct gccaacccgg atcaccctaa    16080
gatctctttc ctaaggggcg agatctaggt tcctacgaga aagaagacga ccctgcacca    16140
ttgcggtccg tccggtccag agtgcgaacg tccggatgcg acacagggaa ggagtcgctc    16200
ctgcagcgag gtcgcagact gtccacacag cctcagaagg caccgccaga caatacatgt    16260
aatacccact ctgtaagaaa aacctaaaag gagaaagtat attcctttat ctatatgtgt    16320
```

-continued

```
gttatatttc tactcaccat cacatgtgaa catctcactt acacaaataa ataattaaca    16380
aaagacactc aaataaatta tgcatcatgc tcgaccttat tttgtgtgca ttctgttaca    16440
atataaaaat aatataaaaa acatatatta atatcaaaat ttggagattt aaccctaata    16500
tgcaaatcgg agtttagagg aaagaaagaa aaatgctata caaaataaag gaataaaatat   16560 ataaataaag gtaaaactat taatactggt atattaattt gaacagttga cctaattatg    16620
aatatcacaa ctggtttgaa ttcaaatatg aaatccaaga atttggaaat aggaaaaatg    16680
gagataagaa taaggaaaaa gaattcttaa ctcggatggg cctgggaaac gaatttcggc    16740
ccacttcctg tgtccttagc tgtgcggctc agtccagtg                          16779
```

```
<210> SEQ ID NO 21
<211> LENGTH: 1307
<212> TYPE: PRT
<213> ORGANISM: Unknown
<220> FEATURE:
<223> OTHER INFORMATION: Acidaminococcus sp.

<400> SEQUENCE: 21

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285
```

```
Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
    595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
    675                 680                 685

Lys Thr Thr Ser Ile Asp Leu Ser Ser Leu Arg Pro Ser Ser Gln Tyr
    690                 695                 700
```

```
Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
            995                 1000                1005

Lys Ala Val Tyr Gln Gln Phe  Glu Lys Met Leu Ile  Asp Lys Leu
       1010                 1015                1020

Asn Cys Leu Val Leu Lys Asp  Tyr Pro Ala Glu Lys  Val Gly Gly
       1025                1030                1035

Val Leu Asn Pro Tyr Gln Leu  Thr Asp Gln Phe Thr  Ser Phe Ala
       1040                1045                1050

Lys Met Gly Thr Gln Ser Gly  Phe Leu Phe Tyr Val  Pro Ala Pro
       1055                1060                1065

Tyr Thr Ser Lys Ile Asp Pro  Leu Thr Gly Phe Val  Asp Pro Phe
       1070                1075                1080

Val Trp Lys Thr Ile Lys Asn  His Glu Ser Arg Lys  His Phe Leu
       1085                1090                1095

Glu Gly Phe Asp Phe Leu His  Tyr Asp Val Lys Thr  Gly Asp Phe
       1100                1105                1110

Ile Leu His Phe Lys Met Asn  Arg Asn Leu Ser Phe  Gln Arg Gly
```

```
                        1115                    1120                    1125
Leu Pro Gly Phe Met Pro Ala Trp Asp Ile Val Phe Glu Lys Asn
                1130                    1135                    1140
Glu Thr Gln Phe Asp Ala Lys Gly Thr Pro Phe Ile Ala Gly Lys
                1145                    1150                    1155
Arg Ile Val Pro Val Ile Glu Asn His Arg Phe Thr Gly Arg Tyr
                1160                    1165                    1170
Arg Asp Leu Tyr Pro Ala Asn Glu Leu Ile Ala Leu Leu Glu Glu
                1175                    1180                    1185
Lys Gly Ile Val Phe Arg Asp Gly Ser Asn Ile Leu Pro Lys Leu
                1190                    1195                    1200
Leu Glu Asn Asp Asp Ser His Ala Ile Asp Thr Met Val Ala Leu
                1205                    1210                    1215
Ile Arg Ser Val Leu Gln Met Arg Asn Ser Asn Ala Ala Thr Gly
                1220                    1225                    1230
Glu Asp Tyr Ile Asn Ser Pro Val Arg Asp Leu Asn Gly Val Cys
                1235                    1240                    1245
Phe Asp Ser Arg Phe Gln Asn Pro Glu Trp Pro Met Asp Ala Asp
                1250                    1255                    1260
Ala Asn Gly Ala Tyr His Ile Ala Leu Lys Gly Gln Leu Leu Leu
                1265                    1270                    1275
Asn His Leu Lys Glu Ser Lys Asp Leu Lys Leu Gln Asn Gly Ile
                1280                    1285                    1290
Ser Asn Gln Asp Trp Leu Ala Tyr Ile Gln Glu Leu Arg Asn
                1295                    1300                    1305
```